United States Patent
Zhao

(10) Patent No.: US 12,421,277 B2
(45) Date of Patent: Sep. 23, 2025

(54) ANTI-AGING SALMON ROE TRIPEPTIDE AND PREPARATION METHOD AND APPLICATION THEREOF

(71) Applicant: Shenzhen Porshealth Bioengineering Co., Ltd., Shenzhen (CN)

(72) Inventor: Tiantian Zhao, Shenzhen (CN)

(73) Assignee: Shenzhen Porshealth Bioengineering Co., Ltd., Shenzhen (CN)

( * ) Notice: Subject to any disclaimer, the term of this patent is extended or adjusted under 35 U.S.C. 154(b) by 0 days.

(21) Appl. No.: 18/651,979

(22) Filed: May 1, 2024

(65) Prior Publication Data

US 2024/0279276 A1      Aug. 22, 2024

(30) Foreign Application Priority Data

Dec. 12, 2023   (CN) .......................... 202311694473.1

(51) Int. Cl.
  *C12P 21/06*  (2006.01)
  *A61K 38/00*  (2006.01)
  *C07K 5/087*  (2006.01)

(52) U.S. Cl.
  CPC ............ *C07K 5/0812* (2013.01); *C12P 21/06* (2013.01); *A61K 38/00* (2013.01)

(58) Field of Classification Search
  None
  See application file for complete search history.

(56) References Cited

U.S. PATENT DOCUMENTS

2014/0242013 A1    8/2014  Yu et al.
2016/0354299 A1*   12/2016 Ershadi .................. A61K 8/365
2018/0255834 A1*   9/2018  Dillmann ............. A24B 15/167
2022/0087926 A1    3/2022  Zou et al.
2022/0347250 A1    11/2022 Chen et al.

OTHER PUBLICATIONS

Merriam-Webster, accessed at https://www.merriam-webster.com/dictionary/antiaging on Jul. 13, 2024, 1 page.*
Kitaeva et al., Int. J. Mol. Sci. 2024, 25, 643, 1-21.*
Li et al. Cell Communication and Signaling (2024) 22: 285; 1-24.*
Tenchov et al. ACS Chem. Neurosci. 2024, 15, 408-446.*
CNIPA, Notification to grant patent right for Chinese application CN202311694473.1, Jan. 16, 2024.

* cited by examiner

*Primary Examiner* — Ilia I Ouspenski
(74) *Attorney, Agent, or Firm* — Hemisphere Law, PLLC; Zhigang Ma

(57) ABSTRACT

The present invention discloses an anti-aging salmon roe tripeptide, having a sequence of YLP. The present invention further discloses a preparation method of the anti-aging salmon roe tripeptide, specifically including the following steps: (1) adding deionized water to salmon roe for homogenization to obtain a salmon roe homogenate; (2) regulating a pH value of the salmon roe homogenate, and adding pancreatin for enzymolysis, enzyme inactivation and cooling to obtain a salmon roe enzymatic hydrolysate; and (3) centrifuging the salmon roe enzymatic hydrolysate, taking a supernatant, and storing the supernatant for later use. A salmon roe peptide prepared by the present invention can increase levels of oxidative stress and skin-related factors (type I collagen and hyaluronic acid) by regulating a cell proliferation state, thereby achieving the protective effect on skin cells on the cell level.

3 Claims, 25 Drawing Sheets

Specification includes a Sequence Listing.

ANTI-AGING SALMON ROE TRIPEPTIDE AND PREPARATION METHOD AND APPLICATION THEREOF

SEQUENCE LISTING

This application contains a Sequence Listing which has been submitted electronically in XML format and is incorporated herein by reference in its entirety. The XML copy named "Sequence Listing XML.XML" was created on Jul. 12, 2025, and is 12,196 bytes in size.

TECHNICAL FIELD

The present invention relates to the technical field of bioactive peptides, and in particular to an anti-aging salmon roe tripeptide and a preparation method and application thereof.

BACKGROUND

Skin aging is the external manifestation of human aging. A mechanism of aging is complex. Studies in recent years have shown that the pathogenesis may be related to many factors, including lipid metabolism, oxidative stress, inflammation, apoptosis, etc. Studies have shown that the main reason for skin aging is that the oxygen free radicals produced by ultraviolet rays and other factors affect the normal growth cycle of skin cells, promote the hydrolysis of collagen and other extracellular matrix by protease, and cause DNA damage and the reduction of matrix protein synthesis, thereby resulting in skin relaxation and reduction of elasticity. With the stimulation of facial muscle fibers by expressions, the most significant sign of skin aging, i.e., wrinkles are produced.

Mechanism of endogenous skin aging: endogenous aging of skin is an irreversible and slow physiological process. Endogenous skin aging is evident only after a certain stage of age, and is characterized by skin drying, roughness, elasticity reduction, and the production of wrinkles. With the increase of age, the dermal mast cells and fibroblasts in the skin tissue are decreased, the secretion of collagen is decreased, and the dermo-epidermal junction area is flattened. Under the influence of aging of other organs in a human body, endogenous skin aging is caused by many factors. From the perspective of the physiological mechanism, oxidative stress causes damage to DNA, protein and other components of cells, and exacerbates progressive telomere shortening, which is an important reason for endogenous skin aging.

Exogenous skin aging: exogenous factors, such as ultraviolet irradiation, pollution and smoking, produce a series of reactions such as pro-oxidation/anti-oxidation through neuroendocrine immune regulation, and affect cell renewal, so as to permanently affect the physiological function of the skin. Ultraviolet induced photoaging is the currently recognized most important cause of skin aging.

Reactive oxygen species (ROS) produced by UV induction can damage DNA and inhibit tyrosine phosphatases, which leads to signal transduction enhancement and ultimately leads to up-regulation of the transcription factor AP-1. At the same time, ultraviolet ray can also lead to the up-regulation of c-Jun as one of the components of AP-1, and down-regulation of retinoic acid receptors, to further weaken the inhibitory effect of retinoic acid on AP-1. Moreover, ultraviolet ray directly induces DNA variation, up-regulates nuclear factor-kB (NF-kB), and inhibits transforming growth factor-$\beta$ (TGF-$\beta$)-mediated cell signaling pathways. These effects lead to degradation or secretion decrease of collagen. Collagen as the most widespread matrix protein of the body provides the support and elasticity for skin. Once the balance of collagen secretion/degradation is broken, the content of collagen in the skin will be reduced, thereby affecting the stability of the skin structure. With the excessive stimulation of the fiber by muscle movement such as expression muscle, the most significant sign of skin aging, i.e., wrinkles are produced. Therefore, the synergistic use of active ingredients with multiple action mechanisms is a preferred choice to achieve a desired anti-aging effect.

Functional extracts separated from aquatic food can be used as functional food and nutritional health products. Peptides obtained from aquatic protein by biotechnology means not only show high nutritional value, but also show biological characteristics for diet or therapeutic purposes, have special active aquatic extracts, and may become functional food for human nutrition. Fish is the earliest biological resource that people begin to eat and rich in protein, vitamins and minerals, and is a high-quality raw material for the development of functional foods such as oligopeptide. At present, a large number of antioxidant, antitumor, antibacterial and anti-inflammatory polypeptides have been obtained by enzymolysis and separation from silver carp, Pacific saury, tilapia and the like, and new structures and mechanisms of action have been continuously discovered. Therefore, rational and efficient development and utilization of freshwater fish resources has broad market prospects, and has certain social and economic significance.

As a kind of popular edible fish, salmon is rich in nutrients, especially Ω3 fatty acids, and is beneficial to heart health and a brain function. Therefore, deep processing of the salmon can not only make full use of resources and achieve high-value utilization, but also increase an added value of the industry and promote sustainable and healthy development of the salmon aquaculture industry.

However, there is no report on use of the salmon roe polypeptide for the anti-aging efficacy.

Therefore, how to provide a salmon roe polypeptide with an anti-aging efficacy is a problem needing to be solved urgently by those of skill in the art.

SUMMARY

In view of this, a purpose of the present invention is to provide an anti-aging salmon roe tripeptide and a preparation method and application thereof, so as to solve the defects in the prior art.

In order to achieve the above purpose, the present invention employs the following technical solution:

An anti-aging salmon roe tripeptide is provided, having a peptide sequence of YLP.

A preparation method of the anti-aging salmon roe tripeptide specifically includes the following steps:
(1) adding deionized water to salmon roe for homogenization to obtain a salmon roe homogenate;
(2) regulating a pH value of the salmon roe homogenate, and adding pancreatin for enzymolysis, enzyme inactivation and cooling to obtain a salmon roe enzymatic hydrolysate;
(3) centrifuging the salmon roe enzymatic hydrolysate, taking a supernatant which is the anti-aging salmon roe tripeptide, and storing the anti-aging salmon roe tripeptide for later use.

Further, in step (1), a mass ratio of the salmon roe to the deionized water is 1:6.

Further, in step (1), for homogenization, a rotating speed is 8000 rpm, and a time is 1 min.

Further, in step (2), an addition amount of the pancreatin is 1%.

Further, in step (2), for enzymolysis, a temperature is 55° C., and a time is 4 h.

Further, in step (2), for enzyme inactivation, a temperature is 90-100° C., and a time is 10-15 min.

Further, in step (2), cooling is performed until a room temperature is reached.

Further, in step (3), for centrifugation treatment, a temperature is 4° C.; a rotating speed is 8000 rpm; and a time is 15 min.

Further, in step (3), a storage temperature is −80° C.

The present invention further requests the protection of application of the salmon roe tripeptide or the salmon roe tripeptide prepared by the above preparation method in the preparation of an anti-aging drug, anti-aging foods, an anti-aging health care product or anti-aging cosmetics.

It can be seen from the above technical solution that compared with the prior art, the present invention has the following beneficial effects:

By evaluating a content of proteins, a degree of hydrolysis, a protein recovery rate, an ABTS antioxidant activity and a tyrosinase inhibitory activity of a salmon roe peptide, the present invention screens preparation conditions with a solid-liquid ratio being 1:6, the addition amount of an enzyme being 1% (according to a mass of a substrate), the enzymolysis time being 4 h, the temperature being 55° C., and the pancreatin selected as a salmon roe peptide-based delivery system; and a content of lipids of the salmon roe peptide is lower than that of an enzymolysis product of salmon, but a content of polyunsaturated fatty acids have an advantage.

A salmon roe peptide prepared by the present invention can increase levels of oxidative stress and skin-related factors (type I collagen and hyaluronic acid) by regulating a cell proliferation state, thereby achieving the protective effect on skin cells on the cell level.

It can be seen from results of an animal experiment, the salmon roe prepared by the present invention can achieve the anti-aging effect by regulating the oxidative stress and a skin state in an aging small water body.

Based on virtual screening means, the present invention finds that the anti-aging tripeptide YLP derived from the salmon can play an important anti-aging role in the body, and has high absorption efficiency, which can play an important role in the body, at the same time.

DETAILED DESCRIPTION

Figure 1:
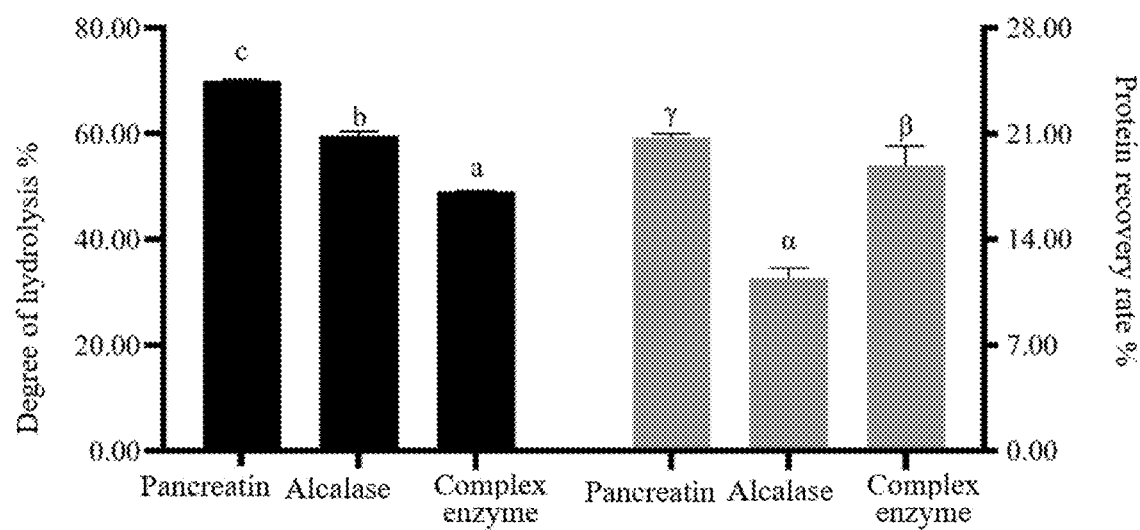
FIG. 1 is a diagram showing degrees of hydrolysis and protein recovery rates according to enzyme types.

Technical solutions in the embodiments of the present invention are described clearly and fully below. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1

A preparation method of an anti-aging salmon roe tripeptide specifically includes the following steps:

(1) adding 6-fold mass of deionized water to salmon roe for homogenization at 8000 rpm for 1 min to obtain a salmon roe homogenate;

(2) regulating the salmon roe homogenate to an optimum pH value; adding 1% pancreatin; placing a mixture in a constant temperature oscillator for enzymolysis at 55° C. for 4 h; then placing a resultant in a boiling water bath for enzyme inactivation at 90° C. for 15 min; and cooling to a room temperature to obtain a salmon roe enzymatic hydrolysate; and (3) centrifuging the salmon roe enzymatic hydrolysate at 4° C. and 8000 rpm for 15 min, taking a supernatant which is the anti-aging salmon roe tripeptide, and storing the anti-aging salmon roe tripeptide at −80° C. for later use.

Embodiment 2

A preparation method of an anti-aging salmon roe tripeptide specifically includes the following steps:
(1) adding 6-fold mass of deionized water to salmon roe for homogenization at 8000 rpm for 1 min to obtain a salmon roe homogenate;
(2) regulating the salmon roe homogenate to an optimum pH value; adding 1% pancreatin; placing a mixture in a constant temperature oscillator for enzymolysis at 55° C. for 4 h; then placing a resultant in a boiling water bath for enzyme inactivation at 95° C. for 12 min; and cooling to a room temperature to obtain a salmon roe enzymatic hydrolysate; and
(3) centrifuging the salmon roe enzymatic hydrolysate at 4° C. and 8000 rpm for 15 min, taking a supernatant which is the anti-aging salmon roe tripeptide, and storing the anti-aging salmon roe tripeptide at −80° C. for later use.

Embodiment 3

A preparation method of an anti-aging salmon roe tripeptide specifically includes the following steps:
(1) adding 6-fold mass of deionized water to salmon roe for homogenization at 8000 rpm for 1 min to obtain a salmon roe homogenate;
(2) regulating the salmon roe homogenate to an optimum pH value; adding 1% pancreatin; placing a mixture in a constant temperature oscillator for enzymolysis at 55° C. for 4 h; then placing a resultant in a boiling water bath for enzyme inactivation at 100° C. for 10 min; and cooling to a room temperature to obtain a salmon roe enzymatic hydrolysate; and
(3) centrifuging the salmon roe enzymatic hydrolysate at 4° C. and 8000 rpm for 15 min, taking a supernatant which is the anti-aging salmon roe tripeptide, and storing the anti-aging salmon roe tripeptide at −80° C. for later use.

Performance Test
I. Process Optimization
1.1 Enzymolysis Process

This research aims to optimize hydrolysis conditions of the salmon roe, so as to obtain a bioactive peptide. An experimental design covers changes of different enzyme types, enzymolysis times, enzyme dosages and solid-liquid ratios.

First, 10 g of the salmon roe is homogenized with ultrapure water at 8000 rpm for 1 min. Then, a resultant is regulated to an optimum pH value, an enzyme is added, and a sample is placed in a constant temperature oscillator for hydrolysis at 55° C. Subsequently, the sample is placed in a boiling water bath for enzyme inactivation at 90-100° C. for 10-15 min. After the sample is cooled to the room temperature, the sample is centrifuged at 4° C. and 8000 rpm for 15 min; and a supernatant is taken to be used for measurement on subsequent indexes, and then stored at −80° C. for later use.

1.2 Single Factor Investigation

Investigation with single factor such as the enzyme type: in a single factor research in terms of the enzyme type, the addition amount of the enzyme is 1%; the hydrolysis time is 4 h; and the solid-liquid ratio is 1:6. Influences of different proteases (pancreatin, Alcalase, and a complex enzyme at a ratio of the pancreatin to the Alcalase being 1:1) on a hydrolysis effect are tested.

Investigation with single factor such as the enzymolysis time: another single factor research aims to determine the influence of the enzymolysis time on formation of a peptide. Under the condition with the solid-liquid ratio being 1:6 and the addition amount of the enzyme being 1%, the pancreatin is used for hydrolysis, and the hydrolysis times of 2 h, 4 h, 8 h, 12 h and 16 h are set separately.

Investigation with single factor such as the addition amount of the enzyme: the influence of the enzyme dosage on a hydrolysis effect is evaluated by means of a single factor research. The solid-liquid ratio is maintained at 1:6, the pancreatin is used for hydrolysis for 4 h, and the dosages of the enzyme added are 0.2%, 0.5%, 0.8%, 1%, and 2% separately.

Investigation with single factor such as the solid-liquid ratio: finally, the influence of the solid-liquid ratio on the hydrolysis effect is explored by means of a single factor research. Salmon roe samples are mixed with 20 mL, 40 mL and 60 mL of water, respectively, and 1% pancreatin is added for hydrolysis for 4 h.

1.3 Measurement on Degree of Hydrolysis and Protein Recovery Rate

The degree of hydrolysis is measured by an OPA method, and the contents of the proteins in the salmon roe and an enzymolysis supernatant are measured by a Kjeldahl method in GB 5009.5-2016 National Food Safety Standard-Determination of Protein in Foods.

Protein recovery rate %=content of proteins in enzymolysis supernatant/content of proteins in salmon roe×100%.

1.4 ABTS Antioxidant Capacity of Enzymolysis Supernatant of Salmon Roe

A measurement method for an ABTS free radical scavenging ability is an experimental method for evaluating an antioxidant capacity of a compound or a sample. ABTS (2, 2'-azino-bis(3-ethylbenzothiazoline) is a synthetic free radical compound that can be used for simulating oxygen free radicals in an organism. The method judges the antioxidant properties by measuring the ABTS free radical scavenging ability of the compound. During measurement, a color of ABTS free radicals will be changed, and addition of an antioxidant substance will lead to fading, and the degree is proportional to the antioxidant capacity. The method includes the basic steps:
① preparation of an ABTS solution: making ABTS reacted with hydrogen peroxide to produce a blue free radical solution, and then diluting to the blue free radical solution with a certain proportion of a solvent to obtain a suitable concentration;
② mixing of a sample to be tested: mixing a compound to be tested with the diluted ABTS solution;
③ measurement on absorbance: in a period of time, determining the ABTS free radical scavenging ability, i.e. the antioxidant capacity, by measuring an absorbance change of a mixture.

In this experiment, the ABTS free radical scavenging ability of the enzymolysis supernatant is measured by referring to an optimized method.

1.5 Tyrosinase Inhibitory Activity
1.5.1 Solution Preparation

L-tyrosine solution: 0.025 g of L-tyrosine is weighed, and added to 50 mL of sterile ionic water; a mixture is dissolved with a phosphate buffer solution with a volume fixed at 50 mL; and the L-tyrosine solution is prepared when needed.

Tyrosinase solution: the tyrosinase is prepared with the phosphate buffer solution until 1000 U/mL; and the tyrosinase solution is stored in the dark at −20° C., and is prepared when needed.

Sample solution: the sample is diluted to a concentration of 1 mg/mL with PBS buffered saline; and the sample solution is prepared when needed.

1.5.2 Test Steps

Referring to amounts of reagents added in Table 1, the L-tyrosine solution, the sample solution/reagent, and the phosphate buffer solution are sequentially added to a reaction system, and fully mixed; a mixture is incubated at a constant temperature of 37° C. for 10 min; then 20 L of the tyrosinase solution is added to wells sequentially for uniform mixing and a reaction at 37° C. for 5 min; a resultant is immediately put into a microplate reader; and the absorbance is tested at 475 nm.

TABLE 1

Sampling Table for Tyrosinase Activity Inhibition Reaction System

| Reagent | Solvent base well ($T_a$) | Solvent reaction well ($T_b$) | Sample base well ($T_c$) | Sample reaction well ($T_d$) |
|---|---|---|---|---|
| L-tyrosine solution (μL) | 0 | 40 | 0 | 40 |
| Sample solution (μL) | 0 | 0 | 40 | 40 |
| Solvent (phosphate buffer solution) (μL) | 40 | 40 | 0 | 0 |
| Phosphate buffer solution (μL) | 70 | 30 | 70 | 30 |

1.6 Experimental Results and Discussion 1.6.1 Single Factor Investigation Results of Salmon 1.6.1.1 Single Factor Investigation Results of Salmon-Enzyme Type The degrees of hydrolysis and the protein recovery rates according to the enzyme types are shown in FIG. 1.

It can be seen from FIG. 1 that the degree of hydrolysis of the pancreatin is the highest, and the protein recovery rates of the salmon roe enzymatically hydrolyzed by different enzymes are as follows: the pancreatin>the complex enzyme>the Alcalase. It can be seen that the protein recovery rate of the salmon roe enzymatically hydrolyzed by the pancreatin is the highest, and enzymolysis of the pancreatin is more effective.

Figure 2:
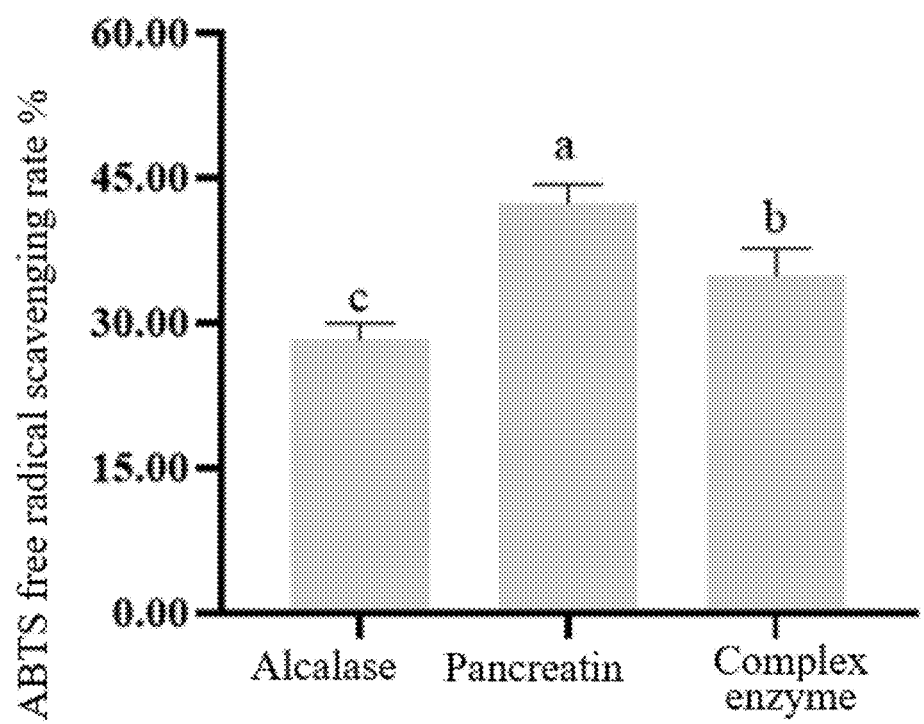
FIG. 2 is a diagram showing ABTS free radical scavenging activities according to enzyme types.

The ABTS free radical scavenging activities according to the enzyme types are shown in FIG. 2.

It can be seen FIG. 2 that the ABTS antioxidant activities of the salmon roe enzymatically hydrolyzed by different enzymes are as follows: the pancreatin>the complex enzyme>the Alcalase. It can be seen that the ABTS antioxidant activity of the salmon roe enzymatically hydrolyzed by the pancreatin is the highest, and the result is positively correlated with the protein recovery rate.

Figure 3:
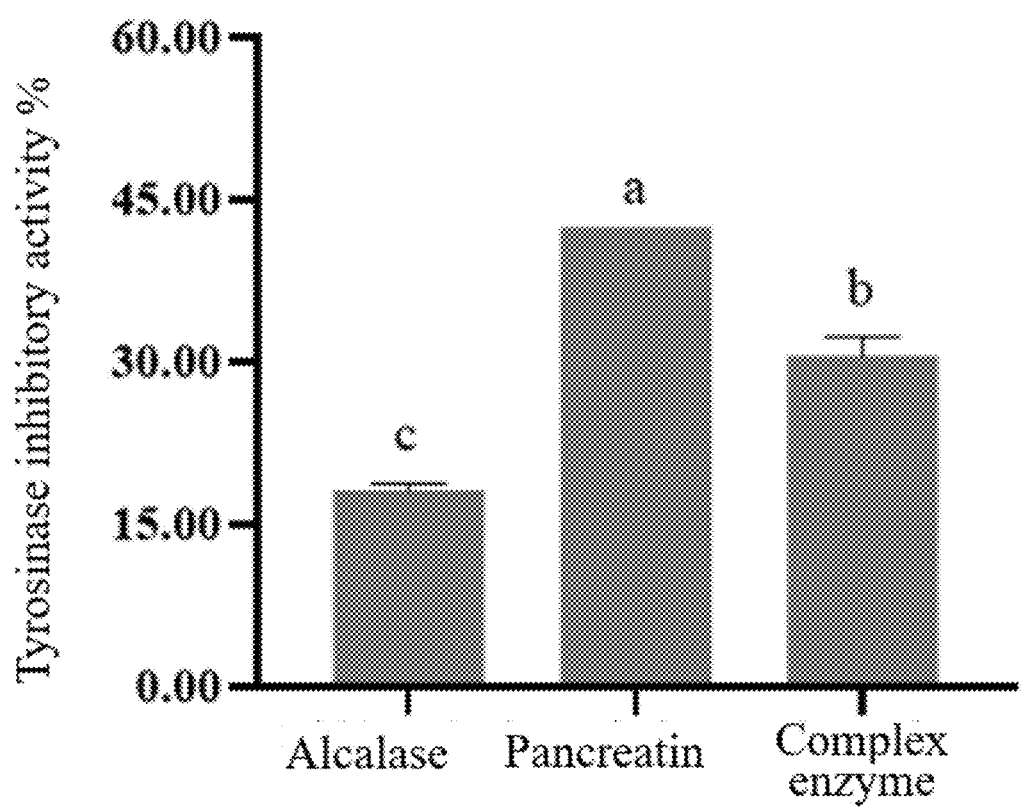
FIG. 3 is a diagram showing tyrosinase inhibitory activities according to enzyme types.

Tyrosinase inhibitory activities according to the enzyme types are shown in FIG. 3.

It can be seen FIG. 3 that the tyrosinase inhibitory activities of the salmon roe enzymatically hydrolyzed by different enzymes are as follows: the pancreatin>the complex enzyme22 the Alcalase. It can be seen that the tyrosinase inhibitory activity of the salmon roe enzymatically hydrolyzed by the pancreatin is the highest, and the result is positively correlated with the protein recovery rate and ABTS antioxidant activity. It can be seen that the tyrosinase inhibitory activity and the ABTS antioxidant activity of the salmon roe enzymatically hydrolyzed by the pancreatin are higher, and enzymolysis of the pancreatin is more full and complete, which is conductive to conservation of a process production cost, and increases bioavailability of the salmon roe. Therefore, the pancreatin is selected for next process optimization.

1.6.1.2 Single Factor Investigation Results of Salmon-Enzymolysis Time

Figure 4:
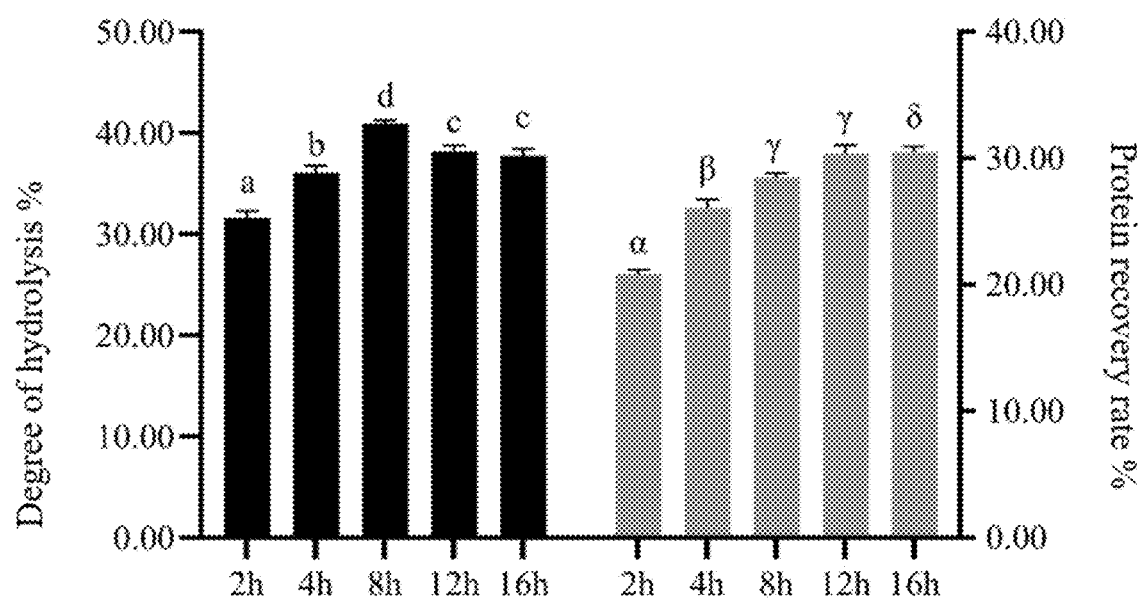
FIG. 4 is a diagram showing degrees of hydrolysis and protein recovery rates under enzymolysis times.

The protein recovery rates and the degrees of hydrolysis under the enzyme hydrolysis times are shown in FIG. 4.

It can be seen FIG. 4 that the protein recovery rate of the salmon roe peptide if the enzymolysis time is 16 h is the highest, followed by 12 h. The salmon roe peptide enzymatically hydrolyzed for 8 h has the highest degree of hydrolysis. Next screening may be performed in combination with the production cost according to the activity.

Figure 5:
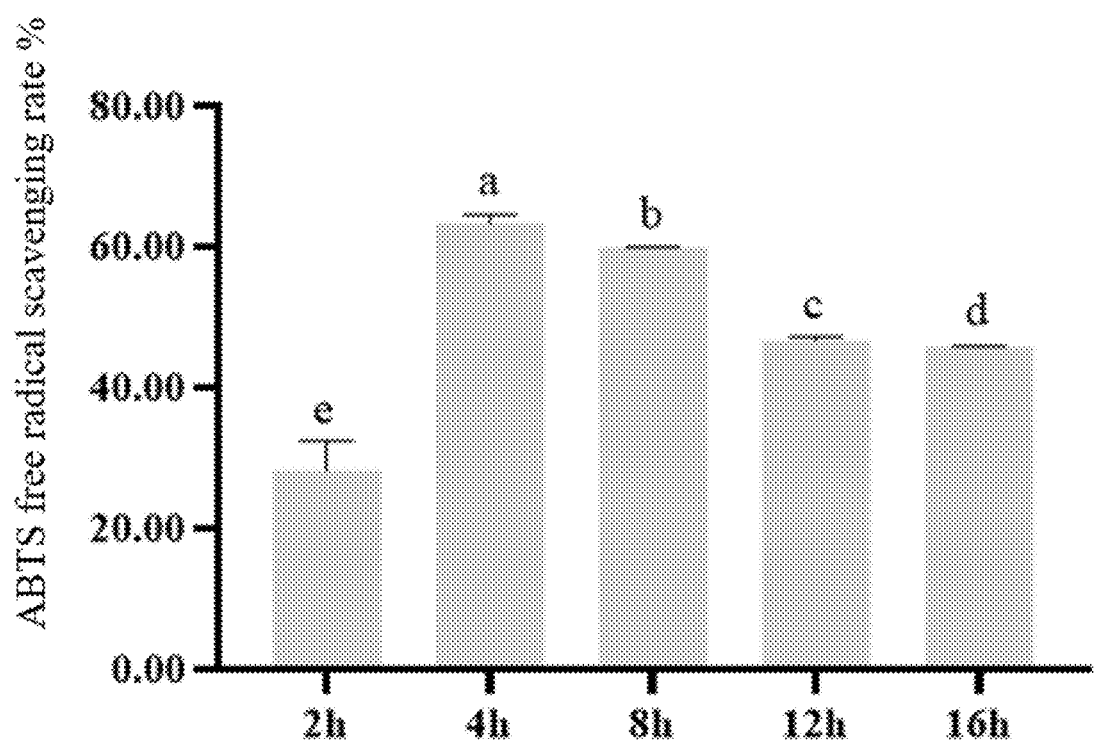
FIG. 5 is a diagram showing ABTS free radical scavenging activities at enzymolysis times.

The ABTS free radical scavenging activities under the enzyme hydrolysis times are shown in FIG. 5.

It can be seen FIG. 5 that the ABTS antioxidant activities under the enzyme hydrolysis times are as follows: 2 h<16 h<12 h<8 h<4 h. The ABTS antioxidant activity of the salmon roe peptide under the enzymolysis time of 4 h is the highest. It is speculated that the enzymolysis time of 4 h can promote release of more antioxidative peptides from the salmon roe during enzymolysis.

Figure 6:
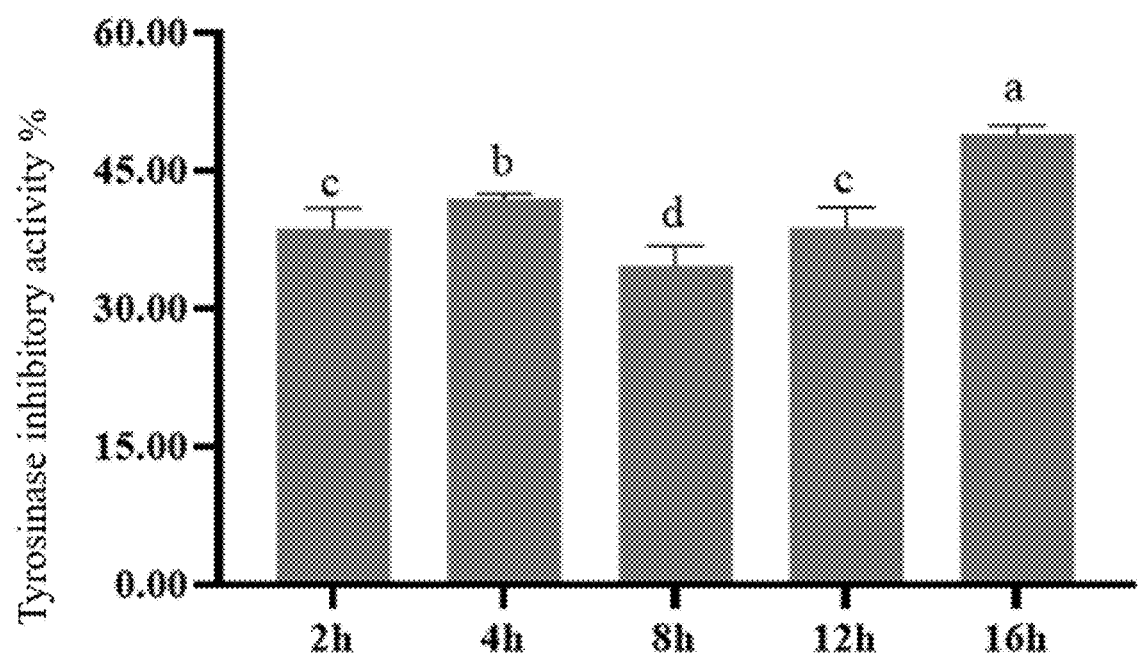
FIG. 6 is a diagram showing tyrosinase inhibitory activities under enzymolysis times.

Tyrosinase inhibitory activities under the enzyme times are shown in FIG. 6.

It can be seen FIG. 6 that through analysis from results under different times, the tyrosinase inhibitory activities under the enzymolysis times are as follows: 8 h<2 h<12 h<4 h<16 h. The tyrosinase inhibitory activity of the salmon roe peptide under the enzymolysis time of 16 h is the highest, followed by 4 h. Combined with the protein recovery rate, the ABTS antioxidant activity, and the production cost, the enzymolysis time of 4 h is selected next for process production.

1.6.1.3 Single Factor Investigation Results of Salmon-Addition Amount of Enzyme

Figure 7:
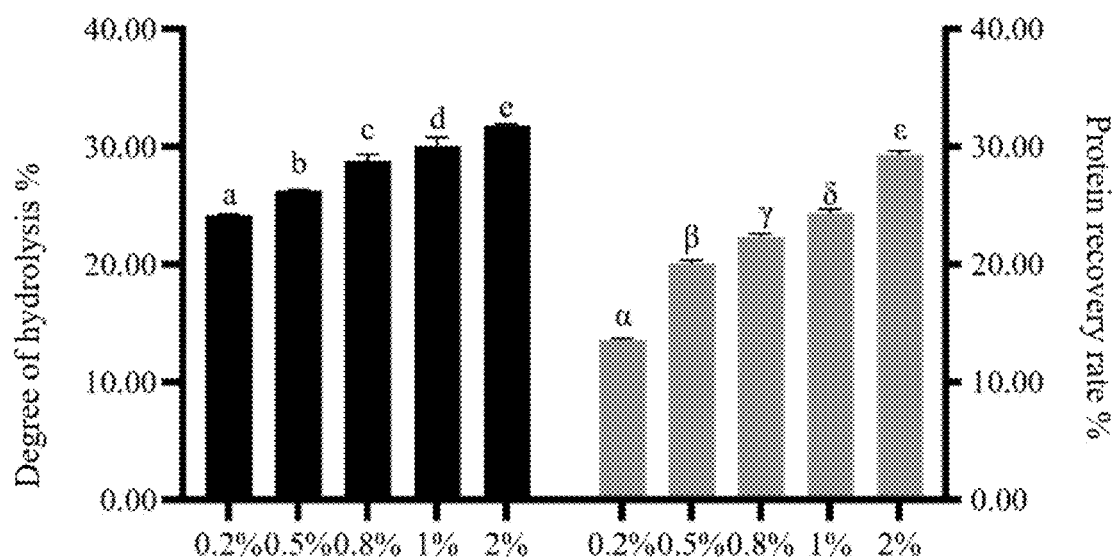
FIG. 7 is a diagram showing degrees of hydrolysis and protein recovery rates at addition amounts of enzyme.

The degrees of hydrolysis and the protein recovery rates at addition amounts of enzyme are shown in FIG. 7.

It can be seen FIG. 7 that the protein recovery rate of the salmon roe peptide is the highest with the addition amount of the enzyme being 2%, and is the lowest with the addition amount of the enzyme being 0.2%. Next screening may be performed in combination with the production cost according to the activity.

Figure 8:
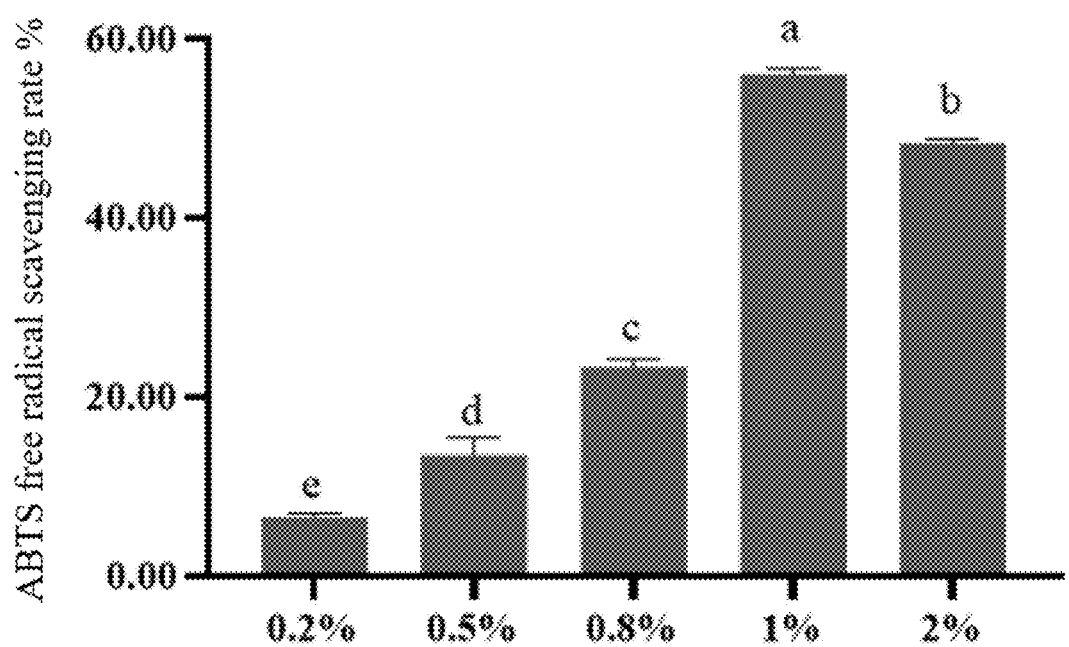
FIG. 8 is a diagram showing ABTS free radical scavenging activities at addition amounts of enzyme.

The ABTS free radical scavenging activities at addition amounts of enzyme are shown in FIG. 8.

It can be seen FIG. 8 that the ABTS antioxidant activity of the salmon roe peptide with the addition amount of the enzyme being 1% is the highest. It is speculated that the addition amount of the enzyme being 1% can promote release of more antioxidative peptides from the salmon roe during enzymolysis.

Figure 9:
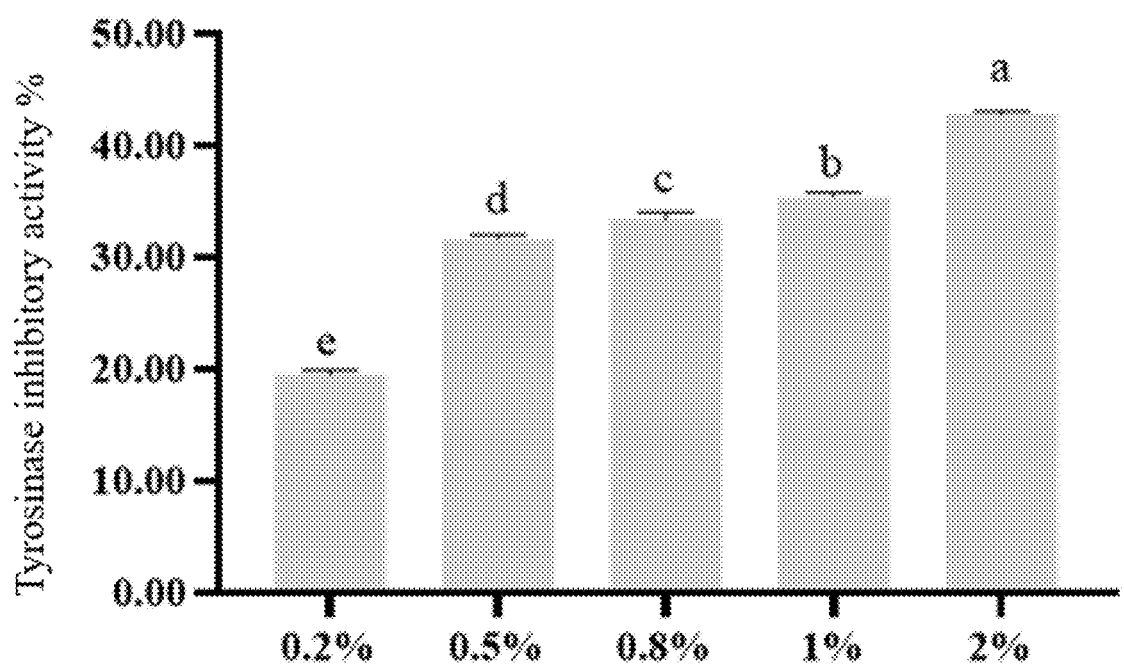
FIG. 9 is a diagram showing tyrosinase inhibitory activities at addition amounts of enzyme.

Tyrosinase inhibitory activities at addition amounts of enzyme are shown in FIG. 9.

It can be seen FIG. 9 that the tyrosinase inhibitory activity of the salmon roe peptide with the addition amount of the enzyme being 2% is the highest, followed by the addition amount of the enzyme being 1%. Combined with the protein recovery rate, the ABTS antioxidant activity, and the production cost, the addition amount of the enzyme being 1% is selected next for process production.

1.6.1.4 Single Factor Investigation Results of Salmon-Solid-Liquid Ratio

Figure 10:
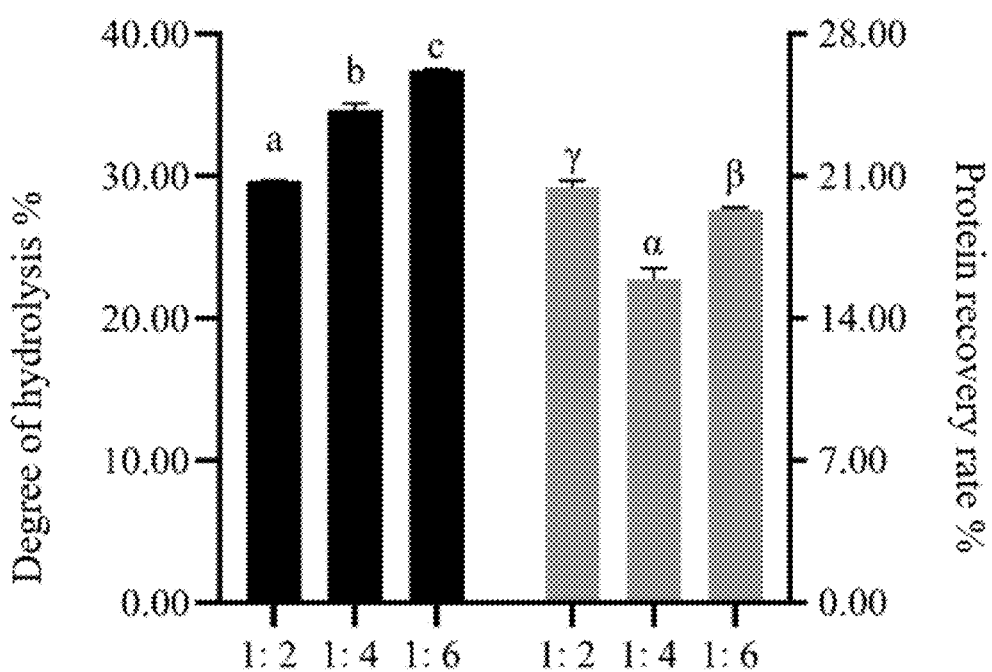
FIG. 10 is a diagram showing degrees of hydrolysis and protein recovery rates at solid-liquid ratios.

The degrees of hydrolysis and the protein recovery rates at solid-liquid ratios are shown in FIG. 10.

It can be seen FIG. 10 that the protein recovery rate of the salmon roe peptide at the solid-liquid ratio of 1:6 is the highest, and the degree of hydrolysis is higher. Next screening may be performed in combination with the production cost according to the activity.

Figure 11:
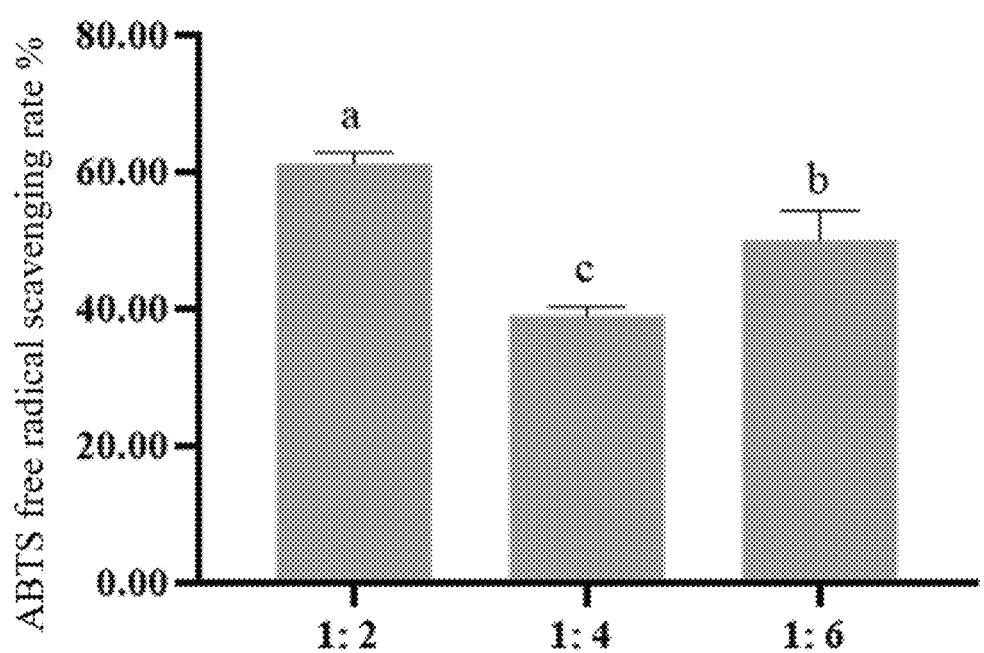
FIG. 11 is a diagram showing ABTS free radical scavenging activities at solid-liquid ratios.

The ABTS free radical scavenging activities at the solid-liquid ratios are shown in FIG. 11.

It can be seen FIG. 11 that an ABTS scavenging rate of the salmon roe peptide at the solid-liquid ratio of 1:2 is the highest. It may be because that the solid-liquid ratio of 1:2 makes the salmon roe peptide have the highest protein recovery rate.

Figure 12:
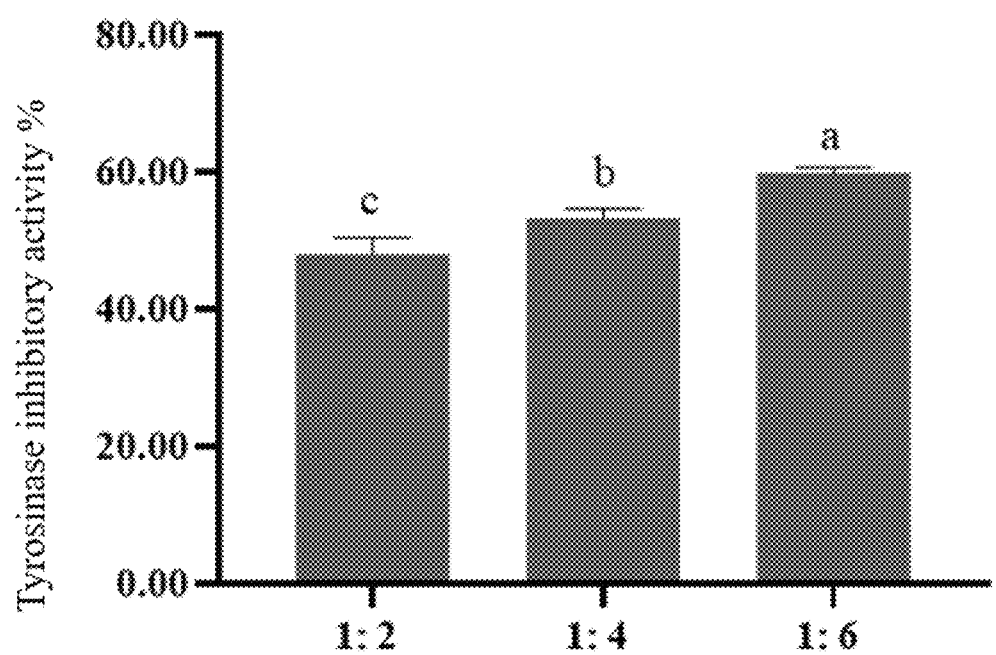
FIG. 12 is a diagram showing tyrosinase inhibitory activities oat solid-liquid ratios.

Tyrosinase inhibitory activities at the solid-liquid ratios are shown in FIG. 12.

It can be seen FIG. 12 that the tyrosinase inhibitory activities of enzymatic hydrolysates at different solid-liquid ratios are as follows: 1:6>1:4>1:2, which is positively correlated with the degree of hydrolysis. It is speculated that as with the increase of the solid-liquid ratio, a surface area of a contact reaction between the salmon roe and the protease is larger, which makes the reaction more full and complete, more salmon roe peptides with the tyrosinase inhibitory activity are released, and the tyrosinase inhibitory activity is enhanced. Combined with the ABTS antioxidant activity and the protein recovery rate, the solid-liquid ratio of 1:6 is selected for next process optimization.

1.7 Analysis on Unsaturated Fatty Acids 1.7.1 Fat Extraction

A 250 mL flat-bottomed flask has a constant weight and is weighed. A sample is weighed and added to a 50 mL colorimetric tube, and 2 mL of 95% ethanol and 4 mL of water are added for uniform mixing. 10 mL of a hydrochloric acid solution is added for uniform mixing. The colorimetric tube is put into a water bath at 70-80° C. for hydrolysis for 40 min. The flask is shaken every 10 min, to make particles adhered to a wall of the flask mixed into the solution. After hydrolysis is completed, the colorimetric tube is taken out, and cooled to the room temperature.

10 mL of the 95% ethanol is added for uniform mixing. 30 mL of an ether/petroleum ether mixed solution is added, and the colorimetric tube is covered. The colorimetric tube is shaken for 5 min, and left for standing for 10 min. An ether layer extract is collected into a 250 mL flask. A hydrolysate is repeatedly extracted for 3 times according to the above steps, the ether layer is evaporated to dryness in a water bath, residues are a fat extract. The flask is put into an oven at 60° C. for drying until a constant weight, and is weighed.

Contents of fats in the salmon roe and a freeze-dried enzymatic hydrolysate are shown in Table 2.

TABLE 2

Contents of Fats in Salmon Roe and Freeze-Dried Enzymatic Hydrolysate

|  | Content of fats/% |
|---|---|
| Salmon roe | 9.60 ± 0.39 |
| Salmon roe freeze-dried hydrolysate | 16.97 ± 1.07 |

1.7.2 Methyl Esterification of Fatty Acids 4 mL of 0.5 µmol/L sodium methoxide is added to a flask, and heated in a water bath at 45° C. for 20 min; a sample solution in the flask is transferred into a 20 mL colorimetric tube; 4 mL of a 14% trifluoro(methanol)boron solution is added; and a mixture is heated in a water bath at 45° C. for 20 min. The mixture is cooled to the room temperature, 3 mL of n-hexane is added for extraction for 2 min; a resultant is left for standing for laying; and then an n-hexane layer is for later test.

1.7.3 Computer Analysis

An initial injection temperature is 100° C., maintained for 13 min, raised to 180° C. at 10° C./min, maintained for 6 min, raised to 192° C. at 1° C./min, maintained for 9 min, raised to 240° C. at 4° C./min, and maintained for 2 min. Operating conditions of a chromatographic column are as follows: an injection volume is 1 µL; a split ratio is 20:1; an injection temperature is 260° C.; a temperature of an ion source is 240° C.; and a SCAN full scan mode is used with a scanning range of 40-400. Results are expressed by g/100 g.

Results of unsaturated fatty acids in the salmon roe and the enzymatic hydrolysate are shown in Table 3.

TABLE 3

Contents of Unsaturated Fatty Acids in Salmon Roe and Enzymatic Hydrolysate

|  | Content of $\Omega3$ fatty acids/% | Content of $\Omega6$ fatty acids/% | Content of $\Omega9$ fatty acids/% |
|---|---|---|---|
| Salmon roe | 3.31 ± 0.29 | 0.67 ± 0.21 | 1.93 ± 0.51 |
| Salmon roe hydrolysate | 6.47 ± 0.16 | 1.21 ± 0.43 | 2.86 ± 0.21 |

By evaluating the content of the proteins, the degree of hydrolysis, the protein recovery rate, the ABTS antioxidant activity and the tyrosinase inhibitory activity of the salmon roe peptide, preparation conditions with the solid-liquid ratio being 1:6, the addition amount of the enzyme being 1% (according to a mass of a substrate), the enzymolysis time being 4 h, the temperature being 55° C., and the pancreatin selected as a salmon roe peptide-based delivery system are screened.

II. Protective Effects of Enzymolysis Sample on HaCaT Cell Oxidative Damage 2.1 Cytotoxicity and Modeling Concentration Selection HaCaT cells in a logarithmic growth phase are taken; a concentration of the cells is regulated to $1.5 \times 10^4$ cells/mL; the cells are inoculated to a 96-well plate, and divided into a normal group and sample groups with different concentration gradients; the normal group is given a blank culture medium; six parallel wells are set for each concentration of a salmon roe extract (with the concentrations of the proteins are 0.1 mg/mL, 0.2 mg/mL, 0.5 mg/mL, 1 and 2 mg/mL respectively); culture is performed for 24 h; and an OD value of each group is measured by a CCK-8 method, and a relative cell viability is calculated.

Relative cell viability % = $OD_{sample}/OD_{normal} \times 100\%$.

The HaCaT cells are inoculated to the 96-well plate at a concentration of $1.5 \times 10^4$ cells per well, with 100 µL per well; adherent culture is performed in an incubator at 37° C. and with 5% $CO_2$ for 24 h; and a culture medium is sucked and discarded. The cells are divided into a normal group and $H_2O_2$ damage groups (0.5 mmol/L, 0.6 mmol/L, 0.7 mmol/L, 0.8 mmol/L, 0.9 mmol/L, 1 mmol/L, 1.1 mmol/L, 1.2 mmol/L, and 1.3 mmol/L); six replicates are set for each group and incubated in 5% $CO_2$ at 37° C. for 2 h; and an OD value of each group is measured by the CCK-8 method, and a relative cell viability is calculated.

$$\text{Relative cell viability \%} = OD_{damage}/OD_{normal} \times 100\%.$$

2.2 Research on Protective Effects of Samples on HaCaT Cells with $H_2O_2$ Damage The HaCaT cells are inoculated to a 96-well plate at a concentration of $1.5 \times 10^4$ cells per well, with 100 μL per well; adherent culture is performed in an incubator at 37° C. and with 5% $CO_2$ for 24 h; and a culture medium is discarded. The cells are divided into a normal group, a model group, and an administration group. The normal group and the model group are given a blank culture medium; and different concentration gradients of samples are added to the administration group. Six replicates are set for each group, and incubated in 5% $CO_2$ at 37° C. for 24 h; and a supernatant is sucked and discarded. Except that the blank culture medium is added to the normal group, 900 μmol/L $H_2O_2$ is added to both the model group and the administration group for a reaction for 6 h. An OD value of each group is measured by the CCK-8 method, and a relative cell viability is calculated.

2.3 Aapoptosis Detection

The HaCaT cells are inoculated to a 6-well plate at a concentration of $6 \times 10^5$ cells per well; adherent culture is performed in an incubator at 37° C. and with 5% $CO_2$ for 24 h; and a culture medium is discarded. The cells are divided into a normal group, a model group, and an administration group. The normal group and the model group are given a blank culture medium; and different concentration gradients of samples are added to the administration group. The cells are incubated in 5% $CO_2$ at 37° C. for 24 h; and a supernatant is sucked and discarded. Except that the blank culture medium is added to the normal group, 900 μmol/L $H_2O_2$ is added to both the model group and the administration group for a reaction for 6 h. The cells are scraped down with a cell scraper, and broken for later use.

300 g of $1.0 \times 10^6$ cells are transferred to a 5 mL flow tube, centrifuged at the room temperature for 5 min; a centrifugate is removed; 2 mL of a binding buffer is added; 300 g of a mixture is centrifuged at the room temperature for 5 min; and a supernatant is removed. The cells are resuspended with 100 μL of a stain buffer; and 5 μL of Annexin V APC and 5 μL of a PI solution are added for incubation at the room temperature for 25 min. 100 μL of the stain buffer is added for computer detection.

2.4 Detection on Oxidative Stress Indexes

A cell treatment method is consistent with that in "2.3 Apoptosis detection". The cells are scraped down with a cell scraper, and broken for later use. Indexes are detected complying with operations of steps of relevant kits for GSH (glutathione), SOD (superoxide dismutase), MDA (malondialdehyde) and LDH (lactate dehydrogenase).

2.5 Cell Scratch Experiment

HaCaT (HDF human dermal fibroblasts inoculated to wells with $1 \times 10^6$ per well) human immortalized epidermal cells are inoculated with $1.2 \times 10^6$ per well. After cell adherence, 200 μL of a gun head is used to draw a straight line in a 6-well plate. The cells are divided into a normal group, a 0.4 mg/mL (the concentration of the proteins) salmon roe extract, and a 0.9 mg/mL (the concentration of the proteins) salmon roe extract. Abasic culture medium is added to the normal group, and sample solutions prepared by the basic culture medium are added to the sampling groups. Cell growth is observed at 0 h, 12 h and 24 h respectively.

2.6 Detection on Type I Collagen and Hyaluronic Acid

HaCaT human immortalized epidermal cells and HDF human dermal fibroblasts are inoculated to a 12-well plate at $3 \times 10^5$ per well. After 24 h of cell adherence, normal culture medium/samples (with two concentration gradients set) are added. After 24 h of culture, a culture supernatant is collected for later test. (A Nanjing Jiancheng human hyaluronic acid (HA) enzyme-linked immunosorbent assay kit, and a human type I collagen (Col I) enzyme-linked immunosorbent assay kit).

2.7 Experimental Results and Discussion 2.7.1 Modeling Concentration Selection

Figure 13:
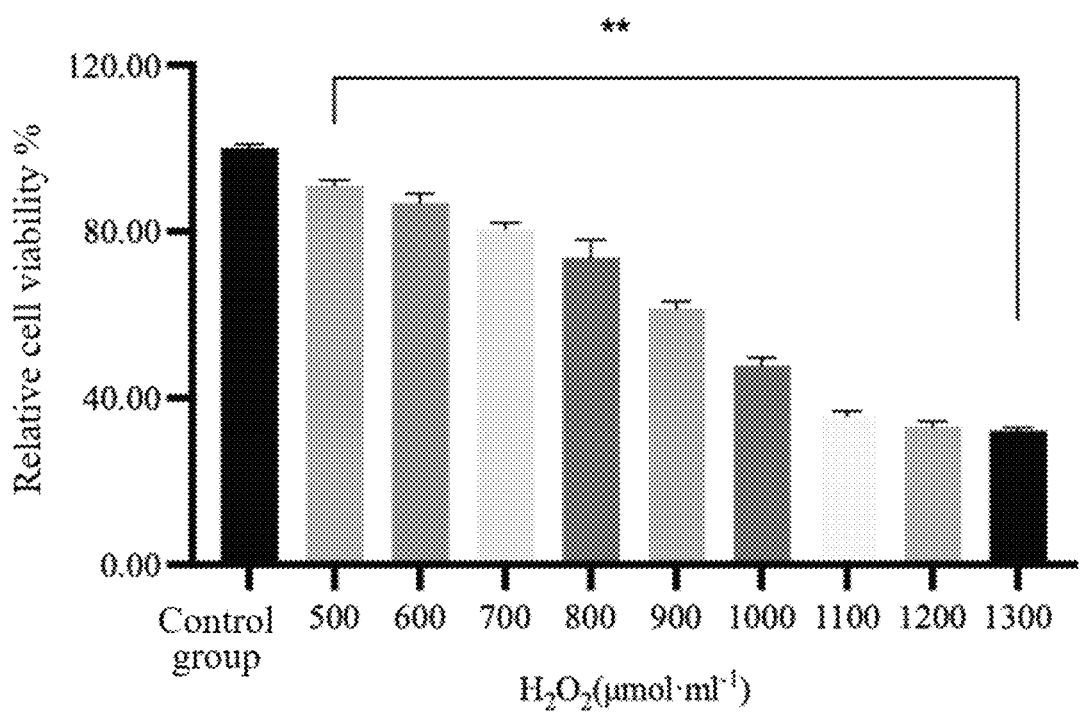
FIG. 13 is a diagram showing modeling concentration screening.

Modeling concentration screening is shown in FIG. 13.

It can be seen from FIG. 13 that during selection of a modeling concentration, if a cell survival rate is too high, a damage is not obvious; and if the cell survival rate is too low, the cells may have serious irreversible damages, which is not conducive to a later experiment. A concentration for the cell viability of 50-70% should be selected as the modeling concentration. When the concentration of $H_2O_2$ reaches 900 μmol/mL, an inhibition rate is 62%. Therefore, this experiment selects the 900 μmol/mL $H_2O_2$ to construct a cell oxidative stress model for a reaction for 6 h, so as to establish an HaCaT cell oxidative damage model.

Figure 14:
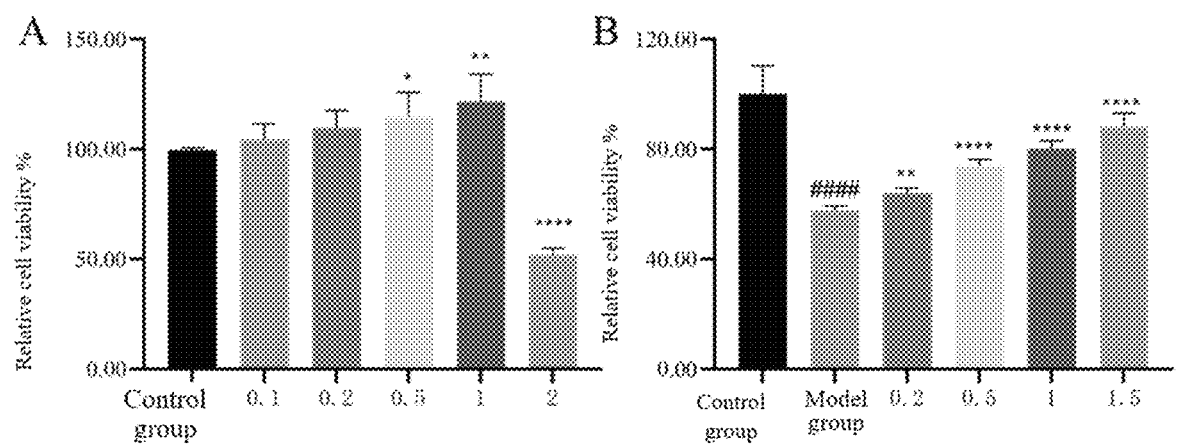
FIG. 14 is a diagram showing protective effects of enzymolysis products of salmon roe on HaCaT cells with $H_2O_2$ damage.

2.7.2 Research on Protective Effects of Enzymolysis Products of Salmon Roe on HaCaT Cells with $H_2O_2$ Damage Results are shown in FIG. 14.

The cytotoxicity of the salmon enzymatic hydrolysate is shown by A in FIG. 14.

It can be seen from A in FIG. 14 that compared with the normal group, when the concentration of the proteins in the salmon roe extract is smaller than or equal to 1 mg/mL, HaCaT cell proliferation is promoted. When the concentration of the proteins in the sample is 2 mg/mL, the sample has a very significant inhibitory effect on the HaCaT cells (P<0.001). From analysis, the reason is that salmon roe raw materials that can be purchased are all pickled, and the very significant inhibitory effect may be caused by salts and ethanol in a product.

The protective effects of the enzymolysis product of the salmon roe on the HaCaT cells with $H_2O_2$ damage are shown by B in FIG. 14.

It can be seen from B in FIG. 14 that there is a very significant difference between a normal group and a model group (P<0.001). With the increase of the concentration of the salmon roe extract, the protective effect on the HaCaT with $H_2O_2$ damage becomes better, and the protective effect is dosage-dependent. When the concentration of the proteins in the salmon roe extract is increased to 0.5 mg/mL, there is a very significant difference between a sample group and the model group (P<0.001).

Figure 15:
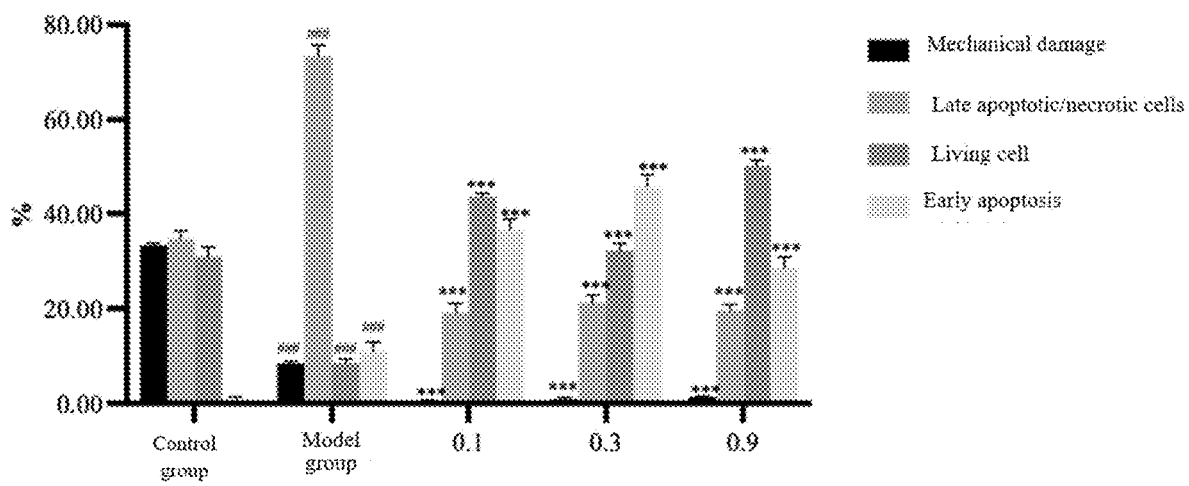
FIG. 15 is a diagram showing protective effects, analyzed by a flow cytometer, of samples on HaCaT cells with $H_2O_2$ damage.

2.7.3 Protective Effects, Analyzed by Flow Cytometer, of Samples on HaCaT Cells with $H_2O_2$ Damage Results are shown in Table 4 and FIG. 15.

TABLE 4

Protective Effects, Analyzed by Flow Cytometer, of Samples on HaCaT Cells with $H_2O_2$ Damage

| Sample | Q2-1% (mechanical damage) | Q2-2% (late apoptosis) | Q2-3% (living cell) | Q2-4% (early apoptosis) | Early + late apoptosis |
|---|---|---|---|---|---|
| Normal group | 33.91% | 35.13% | 30.15% | 0.81% | 35.94% |
| Model group | 8.66% | 71.52% | 8.45% | 11.37% | 82.89% |
| Salmon 0.1 | 0.63% | 16.87% | 43.68% | 38.82% | 55.69% |

TABLE 4-continued

Protective Effects, Analyzed by Flow Cytometer, of Samples on HaCaT Cells with $H_2O_2$ Damage

| Sample | Q2-1% (mechanical damage) | Q2-2% (late apoptosis) | Q2-3% (living cell) | Q2-4% (early apoptosis) | Early + late apoptosis |
|---|---|---|---|---|---|
| Salmon 0.4 | 0.89% | 24.76% | 31.34% | 43.01% | 67.77% |
| Salmon 0.9 | 1.37% | 19.47% | 50.06% | 29.09% | 48.56% |

It can be seen from Table 4 that different quadrants of the flow cytometer represent different states of the cells.

It can be seen from FIG. 15 that in an experiment of the salmon protecting the HaCaT cells from being damaged by $H_2O_2$, a number of late apoptotic cells in the model group is significantly larger than that in a control group (P<0.05), and a number of living cells in the model group is significantly smaller than that in the control group (P<0.05). When the contents of the proteins in the salmon enzymatic hydrolysate are 0.1 mg/mL, 0.3 mg/mL, and 0.9 mg/mL, a number of late apoptotic cells is significantly smaller than that in the model group, and a number of the living cells is significantly larger than that in the model group, wherein the best effect is provided at 0.9 mg/mL.

Figure 16:
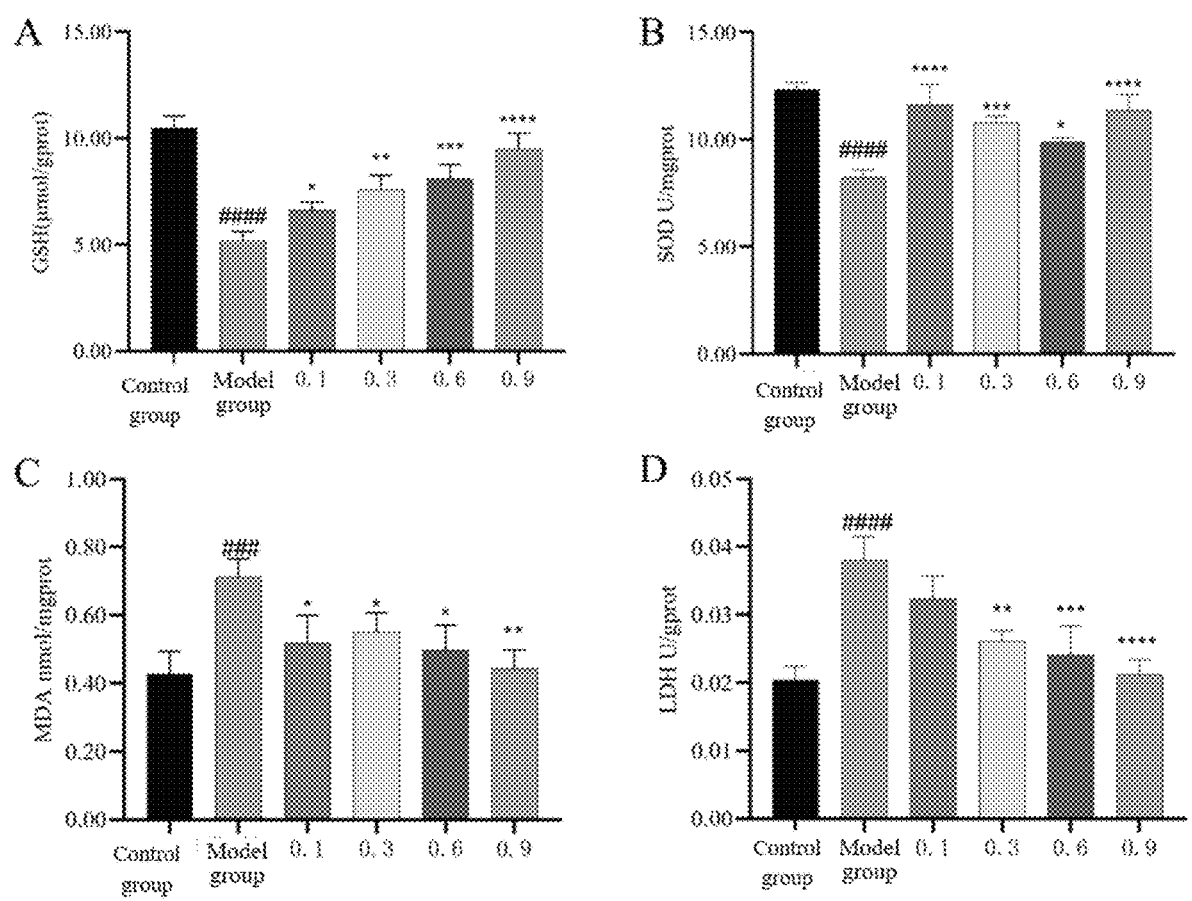
FIG. 16 is a diagram showing influences of enzymolysis products of salmon roe on oxidative stress level of damaged cells.

2.7.4 Influences of Enzymolysis Products of Salmon Roe on Oxidative Stress Level of Damaged Cells Results are shown in FIG. 16.

(1) Influences of Enzymolysis Products of Salmon Roe on Level of Glutathione (GSH) in Damaged Cells As a coenzyme of a variety of enzymes such as GSH-Px, GSH is involved in removal of HO, $O^{2-}$, $H_2O_2$, etc., and can effectively protect a body from being damaged by oxidative stress. Therefore, an amount of the GSH can reflect the body's antioxidant capacity to a certain extent.

The influences of the salmon enzymatic hydrolysates on a level of the glutathione (GSH) in the damaged cells are shown from A in FIG. 16.

It can be seen from A in FIG. 16 that a content of the GSH in a control group is significantly larger than that in a model group (P<0.05). The contents of the GSH in different-concentration sample groups are significantly increased, that is, the antioxidant capacity of a sampling group is strengthened, wherein with the increase of the concentration of the salmon roe extract, the content of the GSH is increased, which is dosage-dependent. When the concentration of the proteins in the salmon roe extract is 0.9 mg/mL, the content of the GSH is the highest.

(2) Influences of Enzymolysis Products of Salmon Roe on Superoxide Dismutase (SOD) in Damaged Cells SOD can convert harmful superoxide free radicals to $H_2O_2$ by means of cellular respiration. A cell damage can lead to a change on the oxidative stress level. In order to further explore the reason, a project team detects an activity of the superoxide dismutase (SOD) in the cells.

The influences of the salmon enzymatic hydrolysates on the superoxide dismutase (SOD) in the damaged cells are shown by B in FIG. 16.

It can be seen from B in FIG. 16 that all salmon roe extract treatment groups can significantly increase the activity of the SOD in the damaged cells (P<0.05); and the salmon roe extract with the concentration of the proteins being 0.1 mg/mL has the strongest ability to improve the activity of the SOD (P<0.001).

It can be seen from results that the salmon roe extract can achieve the purpose of improving the oxidative stress state of the cells by improving the activity of the SOD.

(3) Influences of Enzymolysis Products of Salmon Roe on Malondialdehyde (MDA) in Damaged Cells Malondialdehyde (MDA) is one of symbolic products of lipid peroxidation, and the content in the organism can directly reflect an oxidation or damage degree of the organism. Therefore, improvement in MDA level of the body is also one of important means to achieve anti-oxidation and maintain cell viability.

The influences of the salmon enzymatic hydrolysates on the malondialdehyde (MDA) in the damaged cells are shown by C in FIG. 16.

It can be seen from C in FIG. 16 that different concentrations of salmon samples can all reduce the contents of the MDA in the cells, wherein the salmon roe extract with the concentration of the proteins being 0.9 mg/mL has the strongest ability to reduce the content of the MDA (P<0.01). It can be seen therefrom that the salmon roe extract can improve the cell state by improving the MDA.

(4) Influences of Enzymolysis Products of Salmon Roe on Lactate Dehydrogenase (LDH) in Damaged Cells Destruction of cell membrane structures caused by apoptosis or necrosis will lead to release of enzymes in cytoplasm into a culture fluid, wherein enzymes include the lactate dehydrogenase (LDH) with a stable enzyme activity. Quantitative analysis on the cytotoxicity can be achieved by detecting the activity of the LDH.

The influences of the salmon enzymatic hydrolysates on the lactate dehydrogenase (LDH) in the damaged cells are shown by D in FIG. 16.

It can be seen from D in FIG. 16 that the contents of the LDH in supernatants of different-concentration sample groups are all smaller than that of the model group; and the content of the LDH in the supernatant is reduced gradually with the increase of the sample concentration. When the concentration of the proteins in the salmon roe sample group is 0.3 mg/mL, the content of the LDH is significantly smaller than that in the model group (P<0.01). When the concentration of the proteins in the salmon roe extract is 0.9 mg/mL, the content of the LDH is the least, and the effect is the best.

Based on the above experimental results, the concentration of the proteins in the salmon roe extract is selected as 0.9 mg/mL for a cell scratch test.

2.7.5 Cell Scratch Experiment

HDF cells are an abbreviation of human dermal fibroblast cells. It is a cell type found in a dermis layer of human skin. It is mainly responsible for synthesis of collagen, elastic fibers and other extracellular matrix molecules to maintain a structure, elasticity and stability of the skin. The HDF cells play an important role in physiological and pathological processes such as skin healing, wound repair, and skin aging. Due to the key role in skin health and diseases, researchers often use the HDF cells to explore cell biology, molecular mechanisms, and pathogenesis of related diseases.

The HaCaT cells are a human skin epithelial cell line, also known as human keratinocyte cells (HaCaT). This cell line is separated and cultured from normal human skin keratoma. The HaCaT cells have a high proliferative activity in in vitro culture, and can be divided continuously to form multi-layer cell accumulation, which is similar to an epidermal layer of the human skin. As they can simulate the characteristics of skin epithelial cells, the HaCaT cells are often used in a skin biological research, such as research on cell proliferation, differentiation, keratogenesis, or skin diseases. They are also widely applied to drug safety evaluation, a cosmetic test and biomedical research, so as to explore the molecular mechanism of the skin health and diseases.

Figure 17:
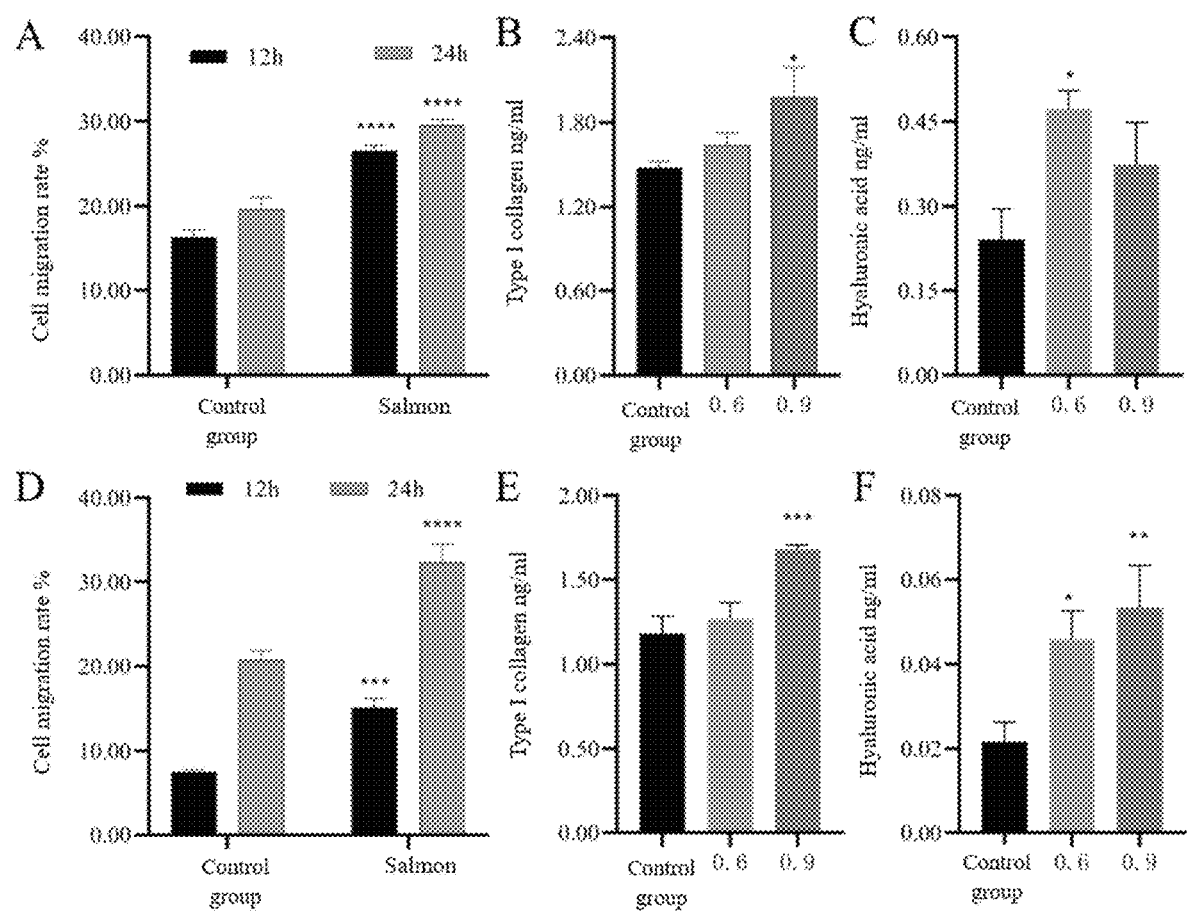
FIG. 17 is a diagram showing results of a cell scratch test.

Results are shown in FIG. 17. The influence of the salmon roe extract on a migration rate of the HaCaT cells is shown by A in FIG. 17. The influence of the salmon roe extract on a content of the type I collagen in the HaCaT cells is shown by B in FIG. 17. The influence of the salmon roe extract on the hyaluronic acid in the HaCaT cells is shown by C in FIG. 17. The influence of the salmon roe extract on the migration rate of the HDF cells is shown by D in FIG. 17. The influence of the salmon roe extract on the content of the type I collagen in the HDF cells is shown by E in FIG. 17. The influence of the salmon roe extract on the hyaluronic acid in the HDF cells is shown by F in FIG. 17.

(1) Influences of Salmon Roe Extract on Migration Rates of HaCaT Cells and HDF Cells It can be seen from A in FIG. 17 and B in FIG. 17 that compared with a control group, salmon samples can significantly increase the migration rates of HaCaT and HDF cells at 0-12 h and 12-24 h (P<0.001).

(2) Influence of Enzymolysis Product of Salmon Roe on Content of Type I Collagen It can be seen from B in FIG. 17 that the HaCaT cells cultured in the salmon samples show a dosage-dependent trend within a specified concentration. The salmon roe extract can significantly increase the content of the type I collagen secreted by the cells (P<0.05) when the concentration of the proteins is 0.9 mg/mL.

It can be seen from E in FIG. 17 that the salmon roe extract can significantly increase the content of the type I collagen in the HDF cells (P<0.001) when the concentration of the proteins is 0.9 mg/mL.

(3) Influence of Enzymolysis Product of Salmon Roe on Content of Hyaluronic Acid It can be seen from C in FIG. 17 that the salmon roe extract can significantly increase the content of the hyaluronic acid secreted by the HaCaT cells (P<0.01) when the concentration of the proteins is 0.6 mg/mL.

It can be seen from F in FIG. 17 that all the sample concentrations can increase the content of the hyaluronic acid in the HDF cells, and the concentration of the proteins in the salmon roe extract is in a dosage-dependent manner when being between 0.6 mg/mL and 0.9 mg/mL. The salmon roe extract can significantly increase the content of the hyaluronic acid in the cells (P<0.05) when the concentration of the proteins is 0.9 mg/mL.

III. Bioactive Polypeptide Sequence Identification and Virtual Screening 3.1 Identification on Sequence of Bioactive Polypeptide in Enzymolysis Product The sample is analyzed by LC-MS/MS equipped with an on-line nano-spray ion source. A total of 3 μL of sample is loaded, and separated in a gradient of 60 min. A column flow rate is controlled at 300 nL/min, a column temperature is 40° C., and an electrospray voltage is 2 kV The gradient starts from a 2% B phase, is increased to 35% in a nonlinear gradient within 47 min, is increased to 100% within 1 min, and is maintained for 12 min.

A mass spectrometer operates in data-dependent acquisition mode, and is automatically switched between MS and MS/MS acquisition. Mass spectrometric parameters are set as follows: (1) MS: scanning range (m/z): 200-2000; resolution: 70,000; AGC target: 3e6; and maximum injection time: 50 ms; and (2) HCD-MS/MS: resolution: 17,500; AGC target: 1e5; maximum injection time: 45 ms; collision energy: 28%; and dynamic exclusion time: 30 s.

Library search parameter settings: a tandem mass spectrum is analyzed by PEAKS Studio version 10.6. PEAKS DB searches a uniprot-Salmo salar or uniprot-Acipenser sinensis database, and sets none enzymolysis. For library search parameters, an allowable error of a fragment ion mass is 0.02 Da, and an allowable error of parent ion mass is 7 ppm. A protein card value contains 1 unique peptide; and a peptide card value is −10 lgP≥20.

3.2 Bioactive Polypeptide Virtual Screening

A database of bioactive peptides and computer virtual screening tools are used to analyze, virtually screen and predict potential bioactive peptides in peptide sequences of the enzymolysis product.

All target polypeptide sequences obtained by the mass spectrometer are used for displaying distribution of the polypeptides in the sample in an Upset Venn diagram.

Peptide Ranker is used to predict and rank the potential biological activities of peptide fragments; and CPPpred is used to predict and rank cell permeability, which can evaluate cell penetration potentials of the peptides. Scores of the above two are between 0 and 1. The higher the score is, the greater the potential is.

A peak area of each peptide represents the content to a certain extent, so the peak area can be used as a filtering condition to improve the accuracy of the identified peptide fragments and screen a main contributor peptide fragment. Therefore, with the Peptide Ranker score>0.5, the CPPpred score>0.1, and a relative peak area>0.05% as the filtering conditions, the potential bioactive peptide is screened out. With the Peptide Ranker score as an x-axis, the CPPpred score as a y-axis, and the peak area of the peptide as an area of a circle, a bubble chart is made to show a relationship among the three.

There is a relationship among a protein function, a charge and hydrophobicity, and a net charge, the hydrophobicity, etc. can be used for describing protein intermolecular force. Researches have found that the hydrophobicity of the proteins has a significant correlation with emulsifying properties, solubility, etc. Therefore, PepDraw is used to measure the chemical properties of the polypeptides: an isoelectric point, the net charge, and the hydrophobicity.

3.3 Results and Discussion 3.3.1 Analysis on Polypeptides in Enzymolysis Products of Salmon Roe By using mass spectrometry and virtual screening methods, combined with peptide ranker, the peak area, CPPpred prediction and other indexes are used for screening the potential bioactive peptides in the enzymolysis products of the salmon roe.

Figure 18:
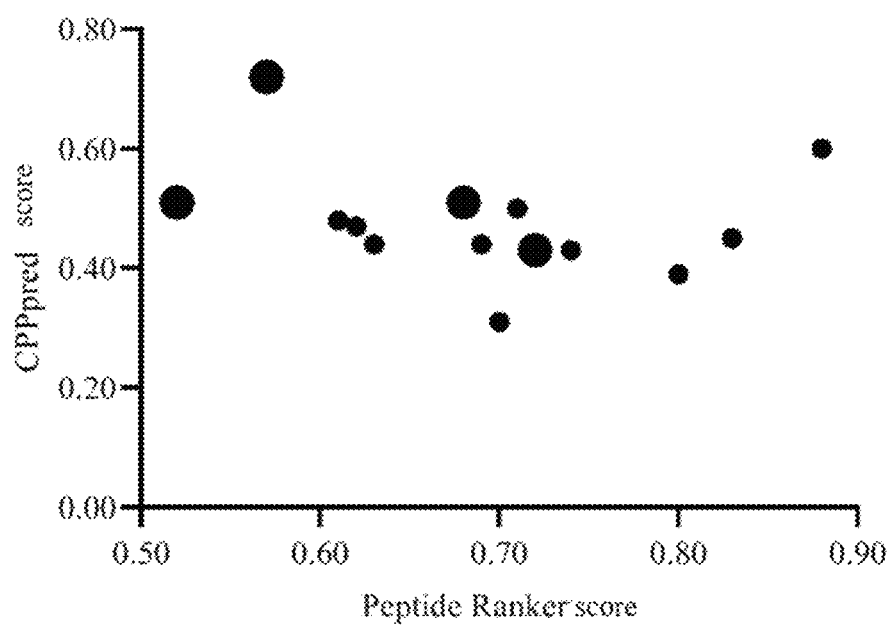
FIG. 18 is a diagram showing scores for polypeptide activities.

Results are shown in Table 5 and FIG. 18.

TABLE 5

| | Peptide Fragments of Salmon | | | | | | |
|---|---|---|---|---|---|---|---|
| Peptide sequence | Peptide Ranker score | Molecular weight (Da) | CPPpred score | Relative peak area (%) | Hydrophobicity (kcal/mol) | Isoelectric point | Net charge |
| YLP | 0.73 | 391.21 | 0.12 | 2.3 | 6.08 | 5.48 | 0 |
| ALPL (SEQ ID NO: 1) | 0.68 | 412.27 | 0.51 | 1.72 | 6.04 | 5.6 | 0 |

TABLE 5-continued

Peptide Fragments of Salmon

| Peptide sequence | Peptide Ranker score | Molecular weight (Da) | CPPpred score | Relative peak area (%) | Hydrophobicity (kcal/mol) | Isoelectric point | Net charge |
|---|---|---|---|---|---|---|---|
| LAW | 0.88 | 388.21 | 0.6 | 0.13 | 5.06 | 5.53 | 0 |
| APARPPPKP (SEQ ID NO: 2) | 0.83 | 929.54 | 0.45 | 0.12 | 14.21 | 11.71 | 2 |
| LGPL (SEQ ID NO: 3) | 0.8 | 398.25 | 0.39 | 0.1 | 6.69 | 5.58 | 0 |
| QRPAQPPQWPAQPPQWPA (SEQ ID NO: 4) | 0.71 | 2079.04 | 10.5 | 0.1 | 11.86 | 11.18 | 1 |
| QWPAQPPQRPA (SEQ ID NO: 5) | 0.74 | 1274.65 | 0.43 | 0.09 | 11.49 | 11.18 | 1 |
| AALPL (SEQ ID NO: 6) | 0.61 | 483.31 | 0.48 | 0.09 | 6.54 | 5.6 | 0 |
| TLFPR (SEQ ID NO: 7) | 0.69 | 632.36 | 0.44 | 0.07 | 7.14 | 10.73 | 1 |
| PAQPLPQRPAQPLPQ (SEQ ID NO: 8) | 0.62 | 1636.9 | 0.47 | 0.07 | 12.13 | 10.8 | 1 |
| QPPQRPAQPPQRPA (SEQ ID NO: 9) | 0.52 | 1566.84 | 0.51 | 0.06 | 16.44 | 12.49 | 2 |
| KPLL (SEQ ID NO: 10) | 0.57 | 469.33 | 0.72 | 0.06 | 8.34 | 10.14 | 1 |
| RLFPT (SEQ ID NO: 11) | 0.72 | 632.36 | 0.43 | 0.06 | 7.14 | 10.79 | 1 |
| ALSDWR (SEQ ID NO: 12) | 0.7 | 746.37 | 0.31 | 0.05 | 10.97 | 6.42 | 0 |
| QRPAQPPQWPAQPP (SEQ ID NO: 13) | 0.63 | 1596.82 | 0.44 | 0.05 | 12.54 | 11.56 | 1 |

It can be seen from Table 5 that in this research, it is obtained that there are 15 polypeptide sequences with the potential biological activity in the enzymolysis product of the salmon roe. Combined with related data such as polypeptide activity scores in FIG. 18, the salmon roe peptide YLP is further selected for a following animal experiment and metabolic experiment.

IV. Animal Experimental Research on Repair Effect of Sample on Aging Mice 4.1 Research on Improvement Effect of Sample on Aging Mice Induced by D-Galactose 4.1.1 Modeling and Intervention In this research, C57BL/6J mice are selected for an experiment, and divided into 8 groups: a normal group, a model group, a low-dosage sample group, a high-dosage sample group, two pure peptide sample groups, and two control groups, with 5 mice in each group. Except for the normal group, from the beginning of the experiment, the mice in the sample groups and the model group are subcutaneously injected with 500 D-galactose solution (125 mg/kg) in the scruff of the necks every day, to establish an aging model for 8 consecutive weeks. The normal group and the control groups receive injection with the same amount of saline. From the 8th d of modeling, the mice in the sample groups are treated with corresponding intragastric samples for 7 consecutive weeks. The control groups and the model group are continued to receive intragastric administration with an equal volume of normal saline. During the experiment, all the mice are fed with a normal feed in an environment of 20-24° C., and operations are performed according to specific dosage indexes.

Specific dosage information is shown in Table 6.

TABLE 6

Animal Experimental Dosage Settings

| Sample | Dosage mg/kg bw | Mg/60 kg |
|---|---|---|
| Salmon polypeptide-L | 75 | 500 |
| Salmon polypeptide-H | 150 | 1000 |
| Salmon YLP | 150 | 1000 |

4.1.2 Index Measurement

In order to evaluate oxidative stress related indexes, 3% pentobarbital sodium (30 mg/kg body weight) is used to perform intraperitoneal anesthesia on the mice 1 h after the last administration, and then blood is collected from orbital venous plexuses of the mice. The obtained blood is stored in a standard blood collection tube, and placed at the room temperature for 1.5 h. Subsequently, the blood is centrifuged at 3000 rpm for 10 min, and a supernatant is taken. The supernatant is used to measure the activities of the superoxide dismutase (SOD), the glutathione (GSH), and the glutathione peroxidase (GSH-Px) and the content of the malondialdehyde (MDA) complying with instructions of the kits.

In addition, in order to measure skin-related biochemical indexes, a skin tissue sample is taken from a hair removal area of a back of each mouse, and it is ensured to remove subcutaneous tissues below it, with a sampling amount of about 0.1 g. The tissue sample is rinsed for 2 times in pre-cooled normal saline, and then water on the surface is dried with filter paper. Then, the tissues are placed in a 4 mL EP tube, and cut into small fragments. Under ice bath conditions, pre-cooled normal saline is added to the tissue fragments (with a final tissue concentration of 0.1 g/mL) for homogenization. Then, a resultant is centrifuged at 12000 rpm for 20 min, and a supernatant is taken. Finally, these supernatants are used to measure the contents of the collagen and the hyaluronic acid (HA) complying with steps of the kits.

4.2 Research on Blood Metabolism of Target Polypeptide 4.2.1 Animal Intragastric Administration In this research, SD rats are used, and divided into three groups: a normal group and salmon YLP groups (with a daily dosage of 100 mg/kg bw). The rats are fasted but allowed to drink water 12 h before the experiment begins. At 15 min, 45 min, 90 min, 180 min and 360 min after intragastric administration, all the rats are anesthetized with the 3% pentobarbital sodium, and blood is collected from abdominal aortas, followed by euthanasia. A polypeptide sample is prepared by solid phase synthesis, and desalted.

4.2.2 Polypeptide Detection 4.2.2.1 Sample Pretreatment (1) The required samples are taken out for thawing, and uniformly mixed by a vortex.
(2) 40 μL of a mixed sample is taken, and 120 μL of methanol is added for shaking treatment for 10 min, and a resultant is centrifuged at a low temperature for 10 min.
(3) 70 μL of a supernatant solution is taken from the centrifuged sample for subsequent measurement.

4.2.2.2 Preparation of Standard Solution

Concentrations of standards are shown in Table 7.

TABLE 7

Concentrations of Standards (unit: ng/mL)

| | SD1 | SD2 | SD3 | SD4 | SD5 | SD6 | SD7 |
|---|---|---|---|---|---|---|---|
| Polypeptide | 0.1 | 0.5 | 1 | 2 | 5 | 10 | 20 |

4.2.2.3 μLC-MS/MS Detection

Chromatographic separation is performed by using a Waters ACQUITY UPLC I-CLASS ultra-high performance liquid chromatographic device. Specific conditions are as follows: chromatographic column Waters UPLC HSS T3 (1.8 m, 2.1 mm×100 mm)—mobile phase: A phase (water, 0.1% formic acid), B phase (methanol)—flow rate: 0.3 mL/min—injection volume: 5.0 μL—column temperature: 40° C.—single sample analysis time: 8 min.

A gradient program of the mobile phases is shown in Table 8.

TABLE 8

Gradient Procedure of Mobile Phases

| Time (min) | A phase (v %) | B phase (v %) |
|---|---|---|
| 0 | 90 | 10 |
| 1 | 90 | 10 |
| 6 | 0 | 100 |
| 6.1 | 90 | 10 |
| 8 | 90 | 10 |

A Waters XEVO TQ-XS tandem quadrupole mass spectrometer is used for mass spectrometry detection. Specific conditions are as follows: positive ion source voltage: 3.0 kV—cone voltage: 30 V—desolvation temperature: 500° C.—desolvation gas flow rate: 1000 μL/h—cone gas flow rate: 150 μL/h.

4.3 Data Preprocessing

Data is expressed in the form of Mean±SD. Graphpad is used for data processing and significance analysis. $P<0.05$ and $P<0.01$ indicate significant and very significant differences in data. A target peak area in polypeptide metabolic data is calculated by using TargetLynx software, and an allowable error of a retention time is 15 s. Concentration calculation is based on a standard curve method to obtain quantitative results.

Figure 19:
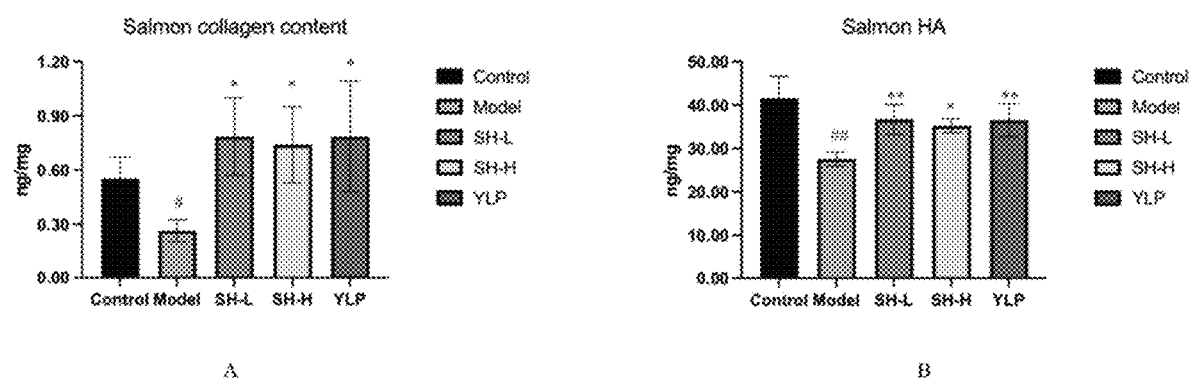
FIG. 19 is a diagram showing influences of enzymolysis products of salmon on skin indexes of aging mice.

4.4 Results and Discussion 4.4.1 Research on Anti-Aging Effect of Enzymolysis Product of Salmon Roe on Aging Mice 4.4.1.1 Influences of Enzymolysis Product of Salmon Roe on Skin Indexes of Aging Mice Results are shown in FIG. 19, wherein A in FIG. 19 and B in FIG. 19 represent the influences of enzymolysis products (SH) of the salmon on the contents of the collagen and the hyaluronic acid in the skin of the aging mice respectively.

It can be seen from A in FIG. 19 that compared with the normal group, after the model group is treated with the D-galactose, the content of the collagen is significantly reduced ($P<0.05$); while low and medium dosages of the enzymolysis products of the salmon can both significantly increase the content of the collagen in the skin of aging mice. ($P<0.05$). The polypeptide YLP obtained from each enzymolysis product of the salmon also shows a significant collagen improvement effect ($P<0.05$).

It can be seen from B in FIG. 19 that compared with the normal group, the content of the hyaluronic acid in the model group is significantly reduced ($P<0.01$), while the salmon enzymolysis product treatment group and the YLP pure peptide groups can significantly increase the content of the hyaluronic acid. The effects of the low-dosage group and the pure peptide groups are better than that of the high-dosage group.

Figure 20:
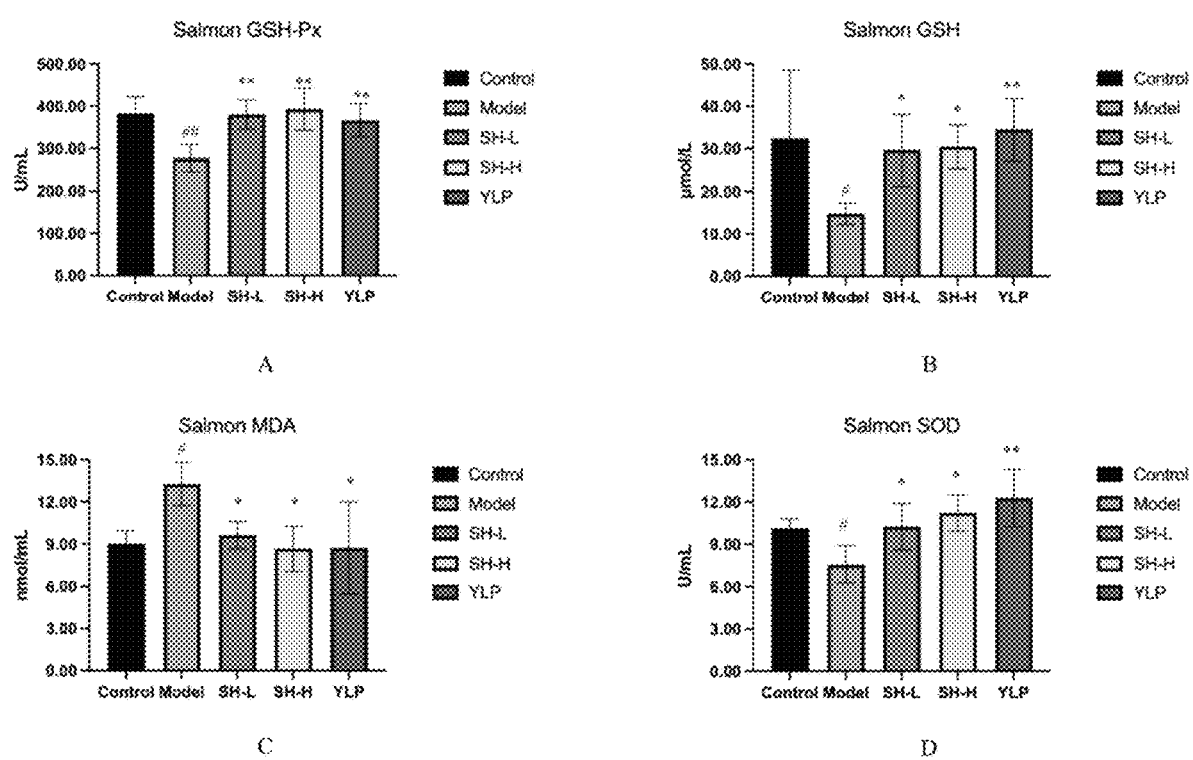
FIG. 20 is a diagram showing influences of enzymolysis products of salmon on blood antioxidant indexes of aging mice.

4.4.1.2 Influences of Enzymolysis Products of Salmon on Blood Antioxidant Indexes of Aging Mice Results are shown in FIG. 20.

Antioxidant indexes can show a body's overall ability to resist aging. It can be seen from A in FIG. 20 that compared with the normal group, the content of the glutathione peroxidase (GSH-Px) in the model group treated with the D-galactose is significantly reduced ($P<0.01$), while different treatment groups can significantly increase the content of the GSH-Px in the aging mice, which shows a positive correlation. Each YLP group also has a significant improvement effect.

The glutathione (GSH) is a recognized antioxidant index. It can be seen from B in FIG. 20 that the content of the glutathione in the model group is significantly reduced, and different treatment groups can all significantly increase the content of the glutathione in the aging mice, especially, each YLP group shows a very significant (P<0.01) improvement effect.

The MDA is a product of lipid peroxidation. An increase in the content of the MDA indicates an increase in lipid oxidation in vivo. It can be seen from C in FIG. 20 that after D-galactose treatment, the content of the MDA in the blood of the model group is significantly increased (P<0.05), while the contents of the MDA in the blood of different treatment groups are significantly reduced (P<0.05).

The SOD is an important index of an antioxidant defense system in vivo. It can be seen from D in FIG. 20 that the activity of the SOD of the model group is significantly reduced (P<0.05), while the salmon enzymolysis product group shows an obvious dosage-dependent improvement effect (P<0.05). YLP pure peptides show a very significant effect on improvement in the activity of the SOD (P<0.01).

In conclusion, the enzymolysis product of the salmon can significantly strengthen the antioxidant system of the aging mice, and shows a dosage-dependent limit. The YLP pure peptides have a good effect on improving the oxidative stress states in the aging mice.

4.4.2 Experiment of Rat Absorbing Salmon Roe Tripeptide (YLP)

4.4.2.1 Polypeptide Standard and Sample Ion Flow

Figure 21:
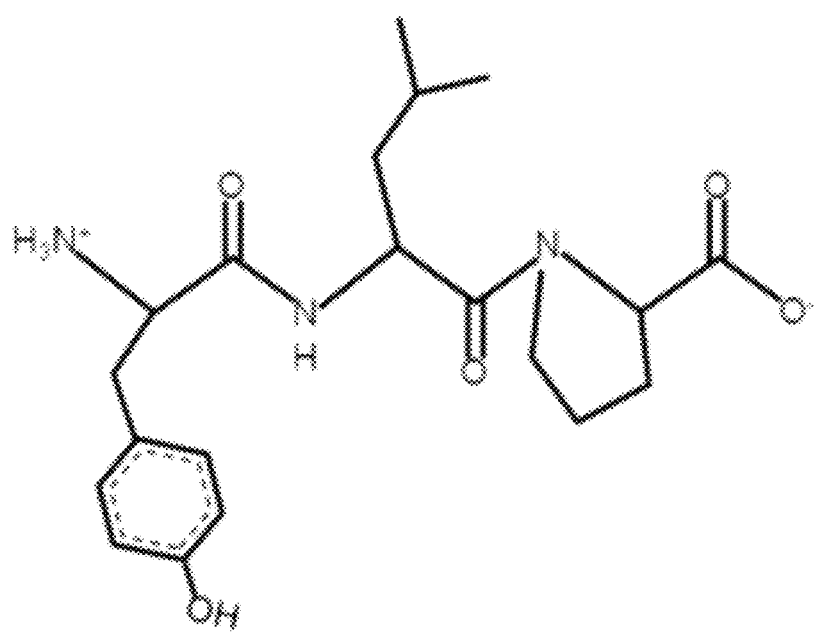
FIG. 21 is a diagram showing a structure of a polypeptide standard.
Figure 22:
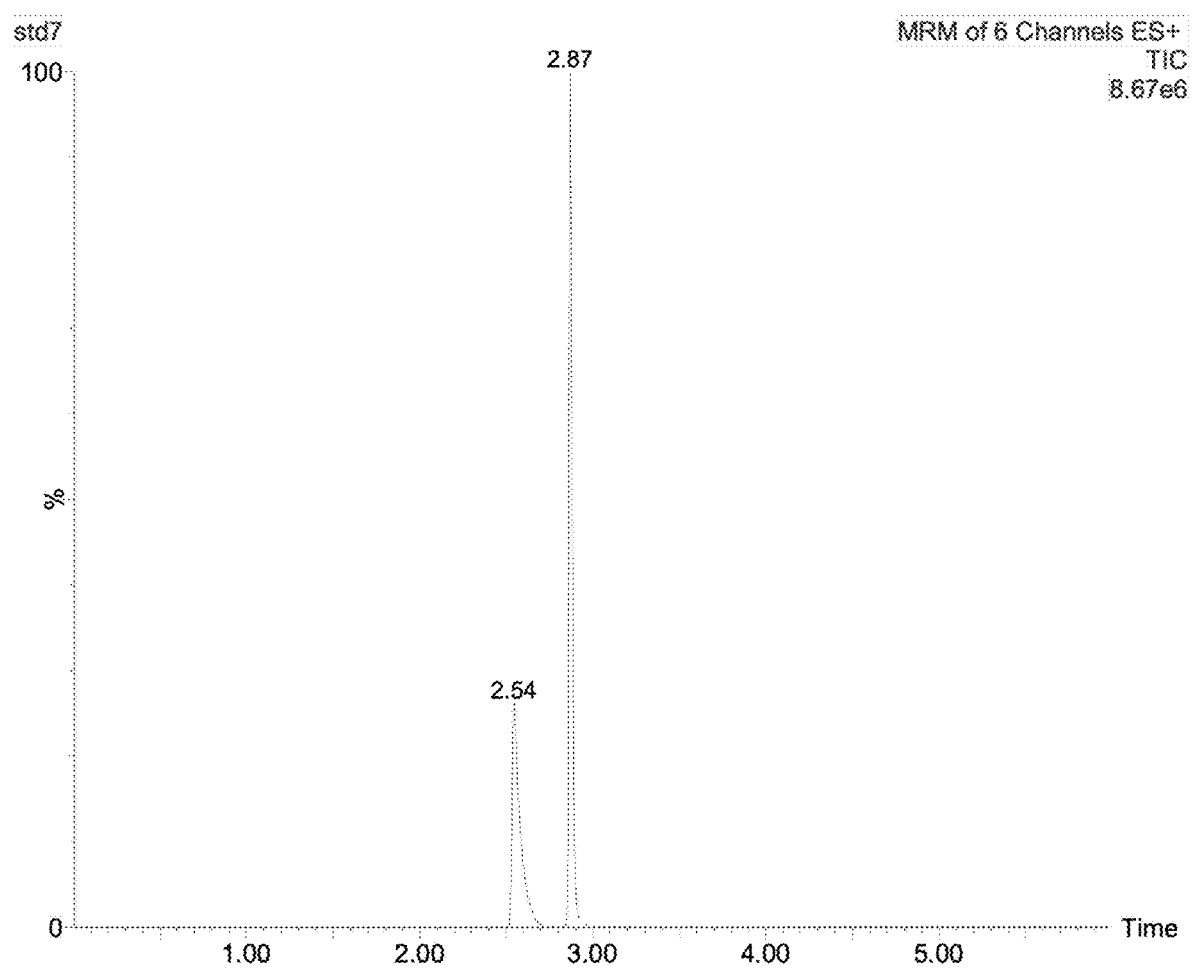
FIG. 22 is a diagram showing a total ion flow of a standard.
Figure 23:
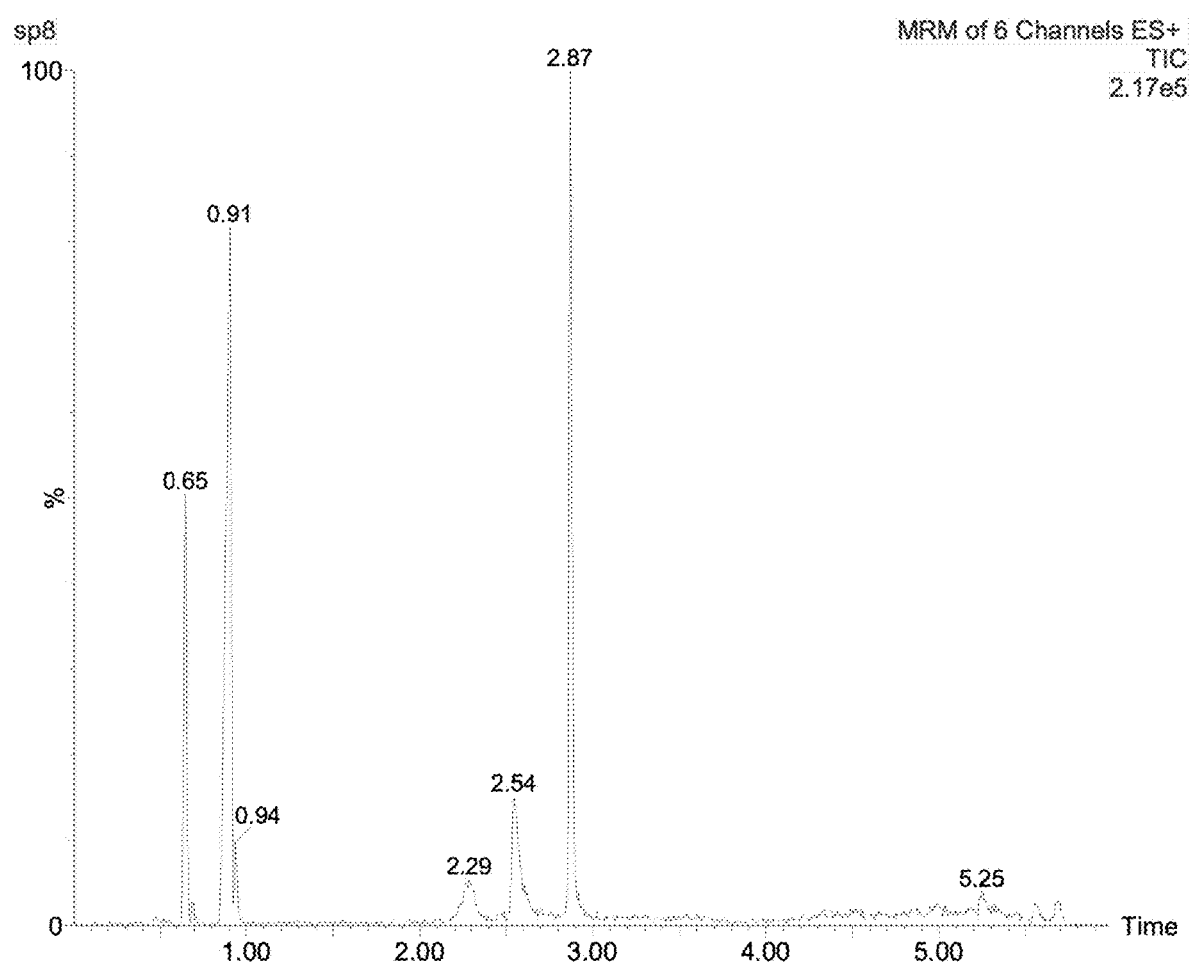
FIG. 23 is a diagram showing a total ion flow of a sample.

Results are shown in FIGS. 21-23. A structure of the polypeptide standard is shown in FIG. 21; a total ion flow of a sample is shown in FIG. 22; and a total ion flow of a sample is shown in FIG. 23.

Figure 24:
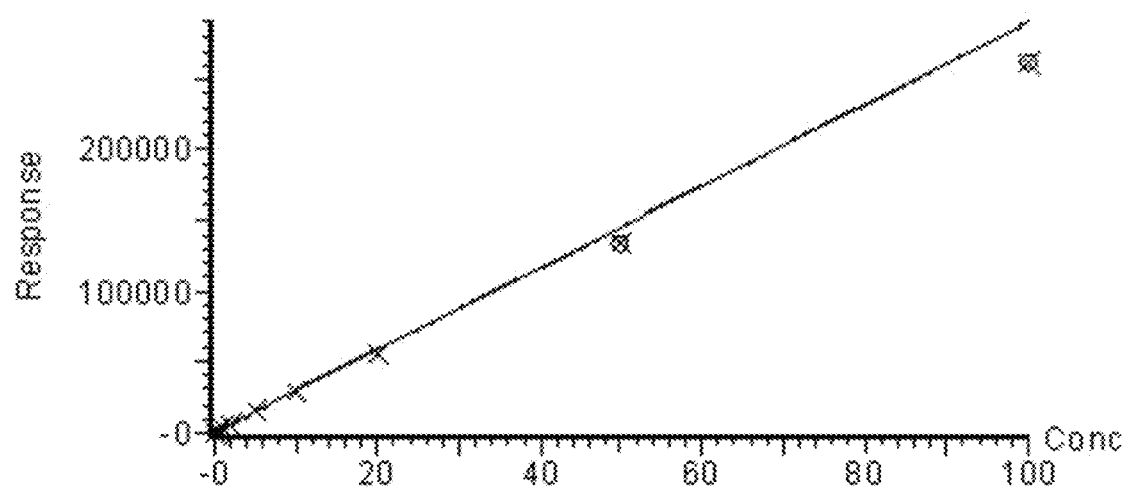
FIG. 24 is a diagram showing a curve of a corresponding standard.

4.4.2.2 Polypeptide Standard Curve and Measurement on Content of Polypeptides in Blood Sample A curve of a corresponding standard is shown in FIG. 24.

It can be seen from FIG. 24 that YLP shows good standard curvilinearity under liquid chromatography-mass spectrometry. $R^2$ is 0.9991, which indicates that the method has high accuracy in measurement on the content of YLP in the sample.

Figure 25:
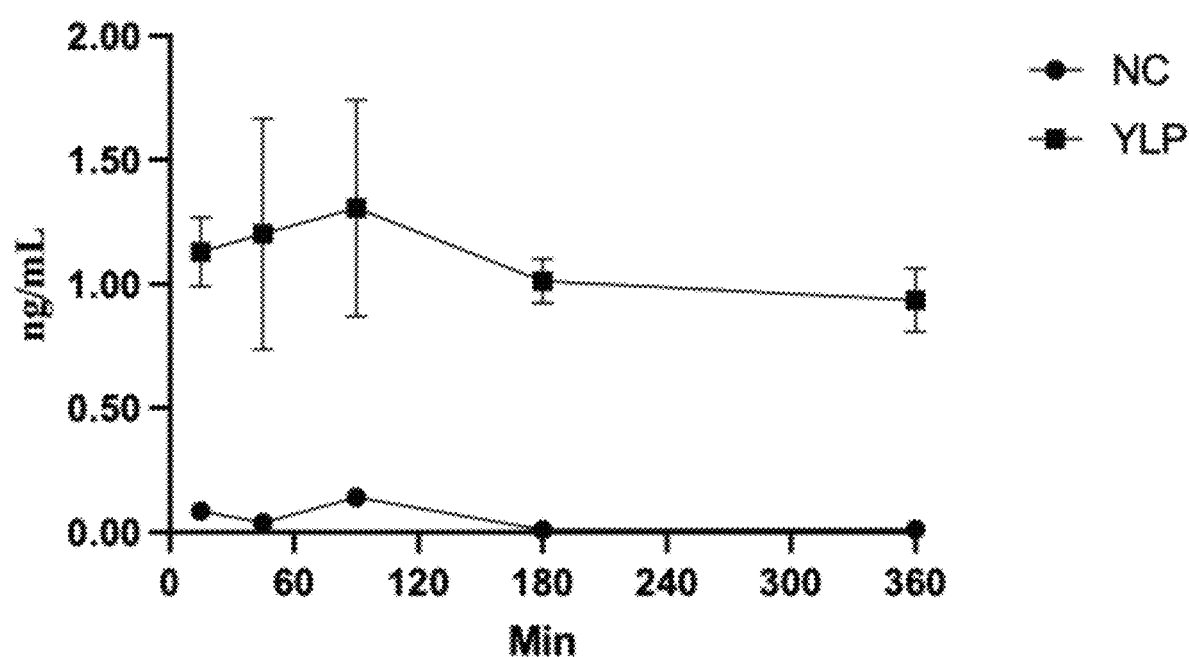
FIG. 25 is a diagram showing in vivo absorption of salmon roe tripeptide YLP.

4.4.2.3 Detection on Contents of Salmon Roe Tripeptide in Rat Blood Sample at Different Time Points In vivo absorption of the salmon roe tripeptide YLP is shown in FIG. 25.

It can be seen from FIG. 25 that a content of YLP tetrapeptide shows a significant upward trend within 90 min, reaches a maximum of 1.31±0.44 ng/mL at 90 min, and shows a downward and regional gentle trend from 90 min to 360 min; and the content is detected at about 1 ng/mL. It can be seen from AUC results, an AUC result of the blank group is 15.04±0.00, and a content of AUC of the YLP group is 371.1±29.16. It can be seen therefrom, compared with the blank group, the content of the YLP in the blood is significantly increased. Combined with the contents in the animal experiment, it can be seen that YLP plays an important role in resisting oxidation and improving skin aging in the aging mice. It can be seen from prediction results of enzyme digestion, during gastrointestinal digestion, YLP may be cleaved into dipeptides such as YL by a gastrointestinal protease. YL has a potential neuroprotective effect, ACE inhibitory activity and DPP-IV enzyme inhibitory activity, can show potential brain nutrition, and regulates blood pressure and blood glucose activities. In this research, the content of YL is not detected.

The above description of the disclosed embodiments enables those skilled in the art to implement or use the present invention. A variety of modifications on these embodiments will be obvious to those skilled in the art. The general principles defined herein can be implemented in other embodiments without departing from the spirit or scope of the present invention. Therefore, the present invention cannot be limited to these embodiments shown herein, but conforms to the widest range consistent with the principle and novel features disclosed herein.

What is claimed is:

1. A preparation method of a salmon roe tripeptide that increases the content of the collagen and hyaluronic acid, wherein a peptide sequence is YLP and the method specifically comprises the following steps:

(1) adding deionized water to salmon roe for homogenization to obtain a salmon roe homogenate;

wherein a mass ratio of the salmon roe to the deionized water is 1:6; for homogenization, a rotating speed is 8000 rpm, and a time is 1 min;

(2) regulating a pH value of the salmon roe homogenate, and adding pancreatin for enzymolysis, enzyme inactivation and cooling to obtain a salmon roe enzymatic hydrolysate;

wherein an addition amount of the pancreatin is 1%;

for enzymolysis, a temperature is 55° C., and a time is 4 h;

(3) centrifuging the salmon roe enzymatic hydrolysate, taking a supernatant which is the anti-aging salmon roe tripeptide, and storing the anti-aging salmon roe tripeptide for later use;

wherein for centrifugation treatment, a temperature is 4° C.; a rotating speed is 8000 rpm; and a time is 15 min.

2. The preparation method of the salmon roe tripeptide according to claim 1, wherein in step (2), for enzyme inactivation, a temperature is 90-100° C., and a time is 10-15 min; and cooling is performed until a room temperature is reached.

3. The preparation method of the salmon roe tripeptide according to claim 1, wherein in step (3), a storage temperature is −80° C.

* * * * *

SEQUENCE LISTING

```
Sequence total quantity: 13
SEQ ID NO: 1            moltype = AA  length = 4
FEATURE                 Location/Qualifiers
source                  1..4
                        mol_type = protein
                        organism = Salmo salar
SEQUENCE: 1
ALPL                                                                    4

SEQ ID NO: 2            moltype = AA  length = 9
FEATURE                 Location/Qualifiers
source                  1..9
                        mol_type = protein
                        organism = Salmo salar
SEQUENCE: 2
APARPPPKP                                                               9

SEQ ID NO: 3            moltype = AA  length = 4
FEATURE                 Location/Qualifiers
source                  1..4
                        mol_type = protein
                        organism = Salmo salar
SEQUENCE: 3
LGPL                                                                    4

SEQ ID NO: 4            moltype = AA  length = 18
FEATURE                 Location/Qualifiers
source                  1..18
                        mol_type = protein
                        organism = Salmo salar
SEQUENCE: 4
QRPAQPPQWP AQPPQWPA                                                     18
```

```
SEQ ID NO: 5              moltype = AA  length = 11
FEATURE                   Location/Qualifiers
source                    1..11
                          mol_type = protein
                          organism = Salmo salar
SEQUENCE: 5
QWPAQPPQRP A                                                                      11

SEQ ID NO: 6              moltype = AA  length = 5
FEATURE                   Location/Qualifiers
source                    1..5
                          mol_type = protein
                          organism = Salmo salar
SEQUENCE: 6
AALPL                                                                              5

SEQ ID NO: 7              moltype = AA  length = 5
FEATURE                   Location/Qualifiers
source                    1..5
                          mol_type = protein
                          organism = Salmo schiefermuelleri
SEQUENCE: 7
TLFPR                                                                              5

SEQ ID NO: 8              moltype = AA  length = 15
FEATURE                   Location/Qualifiers
source                    1..15
                          mol_type = protein
                          organism = Salmo salar
SEQUENCE: 8
PAQPLPQRPA QPLPQ                                                                  15

SEQ ID NO: 9              moltype = AA  length = 14
FEATURE                   Location/Qualifiers
source                    1..14
                          mol_type = protein
                          organism = Salmo salar
SEQUENCE: 9
QPPQRPAQPP QRPA                                                                   14

SEQ ID NO: 10             moltype = AA  length = 4
FEATURE                   Location/Qualifiers
source                    1..4
                          mol_type = protein
                          organism = Salmo salar
SEQUENCE: 10
KPLL                                                                               4

SEQ ID NO: 11             moltype = AA  length = 5
FEATURE                   Location/Qualifiers
source                    1..5
                          mol_type = protein
                          organism = Salmo salar
SEQUENCE: 11
RLFPT                                                                              5

SEQ ID NO: 12             moltype = AA  length = 6
FEATURE                   Location/Qualifiers
source                    1..6
                          mol_type = protein
                          organism = Salmo salar
SEQUENCE: 12
ALSDWR                                                                             6

SEQ ID NO: 13             moltype = AA  length = 14
FEATURE                   Location/Qualifiers
source                    1..14
                          mol_type = protein
                          organism = Salmo salar
SEQUENCE: 13
QRPAQPPQWP AQPP                                                                   14
```